US012751859B2

(12) United States Patent
Jarrett et al.

(10) Patent No.: US 12,751,859 B2
(45) **Date of Patent: *Oct. 6, 2026**

(54) INTRACANALICULAR DEPOT INSERTER DEVICE

(71) Applicant: OCULAR THERAPEUTIX, INC., Bedford, MA (US)

(72) Inventors: Peter Jarrett, Burlington, MA (US); Erik Wong, Newton, MA (US)

(73) Assignee: Ocular Therapeutix, Inc., Bedford, MA (US)

( * ) Notice: Subject to any disclaimer, the term of this patent is extended or adjusted under 35 U.S.C. 154(b) by 116 days.

This patent is subject to a terminal disclaimer.

(21) Appl. No.: 18/619,321

(22) Filed: Mar. 28, 2024

(65) Prior Publication Data

US 2024/0390183 A1 Nov. 28, 2024

Related U.S. Application Data

(63) Continuation of application No. 18/278,538, filed as application No. PCT/US2022/017493 on Feb. 23, 2022, now Pat. No. 12,023,276.

(Continued)

(51) Int. Cl.
*A61F 9/00* (2006.01)
*A61F 9/007* (2006.01)

(52) U.S. Cl.
CPC .................................. *A61F 9/0017* (2013.01)

(58) Field of Classification Search
CPC ...... A61F 9/0017; A61F 9/00772; A61F 2/14; A61F 2/148
See application file for complete search history.

(56) References Cited

U.S. PATENT DOCUMENTS 5,283,063 A 2/1994 Freeman
5,334,137 A 8/1994 Freeman (Continued)

FOREIGN PATENT DOCUMENTS

CN 108852614 A 11/2018
CN 110051468 A 7/2019

(Continued)

OTHER PUBLICATIONS

Supplemental Partial European Search Report of International Application No. PCT/US2022017493 mailed Nov. 27, 2024, 14 pgs.

(Continued)

*Primary Examiner* — Laura A Bouchelle
(74) *Attorney, Agent, or Firm* — Lowenstein Sandler LLP

(57) ABSTRACT

Disclosed in certain embodiments is an intracanalicular injectable applicator device includes a body forming a cavity and a cannula coupled to a first distal end of the body. The cannula forms a channel that is aligned with the cavity of the body. The cannula is configured to store an intracanalicular injectable in the channel. The intracanalicular injectable applicator device further includes a tip structure coupled to the body. The tip structure is disposed around at least a portion of the cannula. A distal end of the tip structure is configured to dilate a lacrimal punctum by inserting the distal end of the tip structure into the canaliculus via the lacrimal punctum. The intracanalicular injectable applicator device further includes an actuating structure configured to push the intracanalicular injectable through the channel and the distal end of the tip structure into a canaliculus via a lacrimal punctum.

20 Claims, 24 Drawing Sheets

Related U.S. Application Data

(60) Provisional application No. 63/250,170, filed on Sep. 29, 2021, provisional application No. 63/153,316, filed on Feb. 24, 2021.

(56) References Cited

U.S. PATENT DOCUMENTS

| | | | | |
|---|---|---|---|---|
| 5,741,292 | A | 4/1998 | Mendius | |
| 6,027,470 | A | 2/2000 | Mendius | |
| 6,041,785 | A | 3/2000 | Webb | |
| 6,234,175 | B1 | 5/2001 | Zhou et al. | |
| 6,344,047 | B1 | 2/2002 | Price et al. | |
| 6,527,780 | B1 * | 3/2003 | Wallace | A61B 17/12022 606/1 |
| 6,629,533 | B1 | 10/2003 | Webb et al. | |
| 6,994,684 | B2 | 2/2006 | Murray et al. | |
| 7,017,580 | B2 | 3/2006 | Prescott et al. | |
| 7,117,870 | B2 | 10/2006 | Prescott | |
| 7,204,253 | B2 | 4/2007 | Mendius et al. | |
| 7,468,065 | B2 * | 12/2008 | Weber | A61F 2/167 606/107 |
| D592,746 | S | 5/2009 | Highley et al. | |
| 8,034,370 | B2 * | 10/2011 | Shiah | A61K 47/34 514/180 |
| 8,252,771 | B2 | 8/2012 | Utecht et al. | |
| 8,377,042 | B2 | 2/2013 | Li et al. | |
| 8,409,606 | B2 | 4/2013 | Sawhney et al. | |
| 8,430,853 | B2 | 4/2013 | Lust | |
| 8,439,865 | B2 | 5/2013 | Lust et al. | |
| 8,563,027 | B2 | 10/2013 | Jarrett et al. | |
| 8,591,484 | B2 | 11/2013 | Gubachy et al. | |
| 8,628,792 | B2 | 1/2014 | Utkhede et al. | |
| 8,668,676 | B2 * | 3/2014 | Chang | A61K 9/1647 604/501 |
| 8,721,322 | B2 | 5/2014 | McAteer et al. | |
| 8,747,884 | B2 | 6/2014 | de Juan, Jr. et al. | |
| 8,808,256 | B2 | 8/2014 | Beaton et al. | |
| 8,821,457 | B2 | 9/2014 | Beeley et al. | |
| 8,894,602 | B2 | 11/2014 | Coldren | |
| 8,911,227 | B2 | 12/2014 | Lust et al. | |
| 8,934,914 | B2 | 1/2015 | Liu | |
| 9,007,540 | B2 | 4/2015 | Nakagawa | |
| 9,011,361 | B2 | 4/2015 | de Juan, Jr. et al. | |
| 9,125,715 | B2 | 9/2015 | Pugh et al. | |
| 9,173,773 | B2 | 11/2015 | Borgia et al. | |
| 9,254,225 | B2 | 2/2016 | Becker | |
| 9,254,267 | B2 | 2/2016 | Sawhney | |
| 9,265,655 | B2 | 2/2016 | Mendius et al. | |
| 9,301,874 | B2 | 4/2016 | Coldren et al. | |
| 9,474,645 | B2 | 10/2016 | Cui et al. | |
| 9,812,730 | B2 | 11/2017 | Otts et al. | |
| 9,849,027 | B2 | 12/2017 | Highley et al. | |
| 9,949,942 | B2 | 4/2018 | Butuner | |
| 11,077,053 | B2 | 8/2021 | Dibas et al. | |
| 11,400,070 | B2 | 8/2022 | Green et al. | |
| 12,023,276 | B2 * | 7/2024 | Jarrett | A61F 9/00772 |
| 2002/0173756 | A1 | 11/2002 | Waldock | |
| 2004/0068235 | A1 | 4/2004 | Hallam | |
| 2004/0068286 | A1 | 4/2004 | Mendius | |
| 2006/0074370 | A1 | 4/2006 | Zhou | |
| 2006/0089384 | A1 | 4/2006 | Minno et al. | |
| 2006/0105941 | A1 | 5/2006 | Schiffman et al. | |
| 2006/0148899 | A1 | 7/2006 | Green et al. | |
| 2008/0038317 | A1 | 2/2008 | Chang et al. | |
| 2008/0045911 | A1 | 2/2008 | Borgia et al. | |
| 2008/0097459 | A1 | 4/2008 | Kammerlander et al. | |
| 2009/0105749 | A1 | 4/2009 | de Juan et al. | |
| 2009/0318549 | A1 | 12/2009 | Butuner | |
| 2010/0040670 | A1 | 2/2010 | Odrich et al. | |
| 2010/0114309 | A1 | 5/2010 | De Juan, Jr. et al. | |
| 2010/0189766 | A1 | 7/2010 | Utkhede et al. | |
| 2010/0209477 | A1 | 8/2010 | Butuner et al. | |
| 2010/0209478 | A1 | 8/2010 | Sawhney | |
| 2010/0243100 | A1 | 9/2010 | Tokarski et al. | |
| 2010/0256578 | A1 | 10/2010 | Lust et al. | |
| 2010/0274224 | A1 | 10/2010 | Jain et al. | |
| 2011/0019317 | A1 | 1/2011 | Vinson | |
| 2011/0150967 | A1 | 6/2011 | Green | |
| 2011/0223170 | A1 | 9/2011 | Stern et al. | |
| 2011/0251568 | A1 | 10/2011 | Beeley et al. | |
| 2011/0301555 | A1 | 12/2011 | Gonzalez-Zugasti et al. | |
| 2011/0311606 | A1 | 12/2011 | Coldren | |
| 2012/0109058 | A1 | 5/2012 | Fukaya | |
| 2012/0157938 | A1 | 6/2012 | Tokarski et al. | |
| 2012/0245539 | A1 | 9/2012 | Zarins et al. | |
| 2013/0018360 | A1 | 1/2013 | Dockendorf et al. | |
| 2013/0090611 | A1 | 4/2013 | Lust et al. | |
| 2013/0123718 | A1 | 5/2013 | Lust et al. | |
| 2013/0220346 | A1 | 8/2013 | Lust et al. | |
| 2013/0226110 | A1 | 8/2013 | Pugh et al. | |
| 2013/0252997 | A1 | 9/2013 | Schiffman | |
| 2014/0107102 | A1 | 4/2014 | Parasrampuria et al. | |
| 2014/0243763 | A1 | 8/2014 | Heikali | |
| 2014/0364891 | A1 | 12/2014 | Mendius et al. | |
| 2016/0206473 | A9 | 7/2016 | Lust et al. | |
| 2018/0177718 | A1 | 6/2018 | Garcia et al. | |
| 2018/0180625 | A1 | 6/2018 | Salinas et al. | |
| 2019/0290488 | A1 | 9/2019 | Gubachy | |
| 2019/0336466 | A1 | 11/2019 | Green et al. | |
| 2021/0205273 | A1 | 7/2021 | Dibas et al. | |
| 2021/0212998 | A1 | 7/2021 | Peters | |
| 2021/0228408 | A1 | 7/2021 | Navratil et al. | |
| 2021/0236809 | A1 | 8/2021 | Ackermann et al. | |
| 2021/0260041 | A1 | 8/2021 | Graham et al. | |
| 2021/0260042 | A1 | 8/2021 | Dibas | |
| 2022/0040152 | A1 | 2/2022 | Abad | |
| 2022/0080049 | A1 | 3/2022 | Garcia et al. | |
| 2022/0288031 | A1 | 9/2022 | Dibas et al. | |

FOREIGN PATENT DOCUMENTS

| | | | |
|---|---|---|---|
| EP | 1305061 | B1 | 3/2004 |
| WO | 2009035567 | A2 | 3/2009 |
| WO | 2012144980 | A1 | 10/2012 |
| WO | 2013013207 | A1 | 1/2013 |
| WO | 20180013869 | A1 | 1/2018 |

OTHER PUBLICATIONS

International Search Report of International Application No. PCT/US2022/017493 mailed May 11, 2022, 12 pgs.

International Search Report of International Application No. PCT/US2022/017493 mailed May 11, 2022, 18 pgs.

* cited by examiner

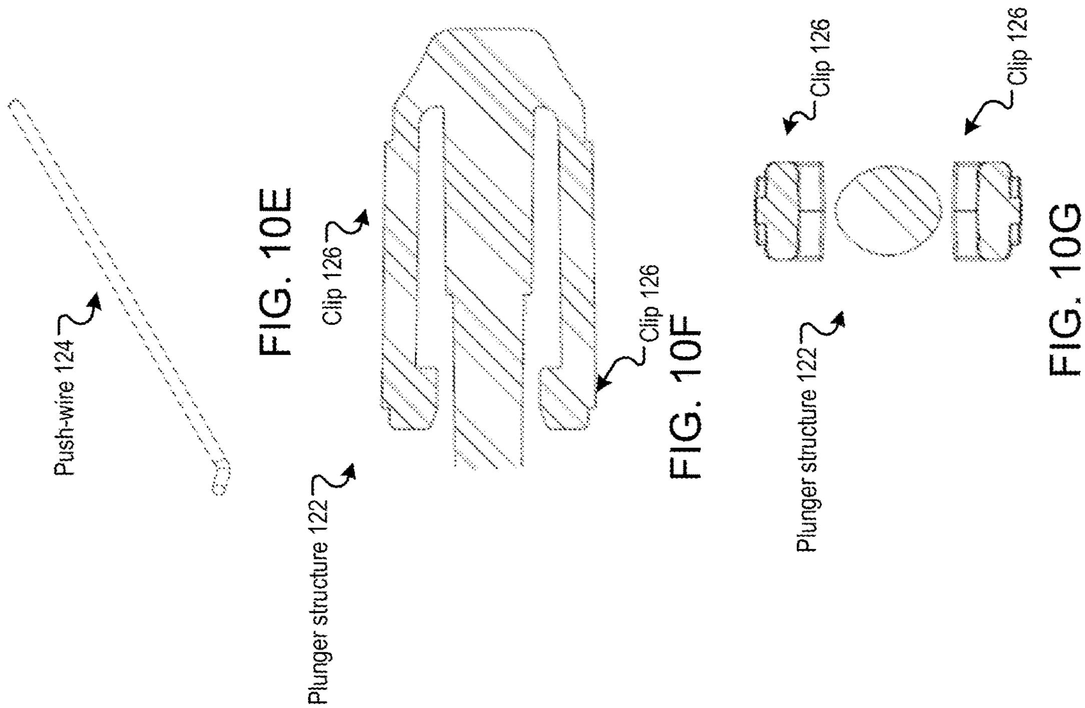
Push-wire 124
FIG. 10E
Clip 126
Plunger structure 122
Clip 126
FIG. 10F
Clip 126
Clip 126
Plunger structure 122
FIG. 10G
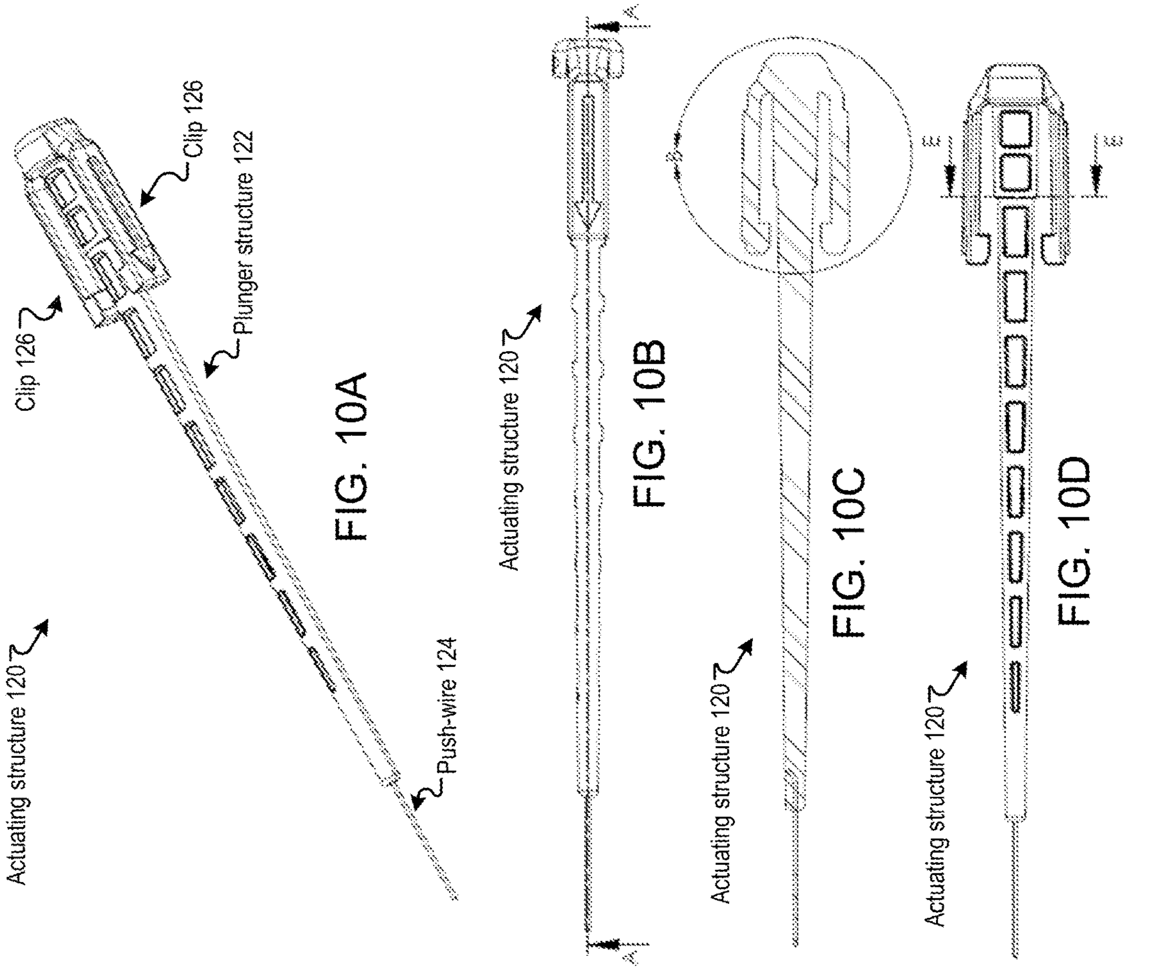
Actuating structure 120
Clip 126
Clip 126
Plunger structure 122
Push-wire 124
FIG. 10A
Actuating structure 120
FIG. 10B
Actuating structure 120
FIG. 10C
Actuating structure 120
FIG. 10D

INTRACANALICULAR DEPOT INSERTER DEVICE

RELATED APPLICATIONS

This application claims benefit of U.S. Provisional Application No. 63/153,316, filed Feb. 24, 2021, and U.S. Provisional Application No. 63/250,170, filed Sep. 29, 2021, the entire contents of which are incorporated by reference in their entirety and for all purposes.

TECHNICAL FIELD

Embodiments of the present disclosure relate to an inserter device, and in particular to an intracanalicular depot inserter device.

BACKGROUND

Lacrimal puncta are minute openings on the margins of the eyelids. The lacrimal punctum leads to a canaliculus. An intracanalicular injectable may be inserted into the canaliculus via the lacrimal punctum. The intracanalicular injectable may be an injectable medication or injectable biologic that is injected by a physician via the lacrimal punctum into a patient. The intracanalicular injectable may be a product that is applicable to the prevention, treatment, or cure of a disease or condition of an eye of a patient.

BRIEF DESCRIPTION OF THE DRAWINGS

The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIGS. 10A-G illustrate actuating structures of intracanalicular injectable applicator devices, according to certain embodiments.

DETAILED DESCRIPTION OF EMBODIMENTS

Figure 1A:
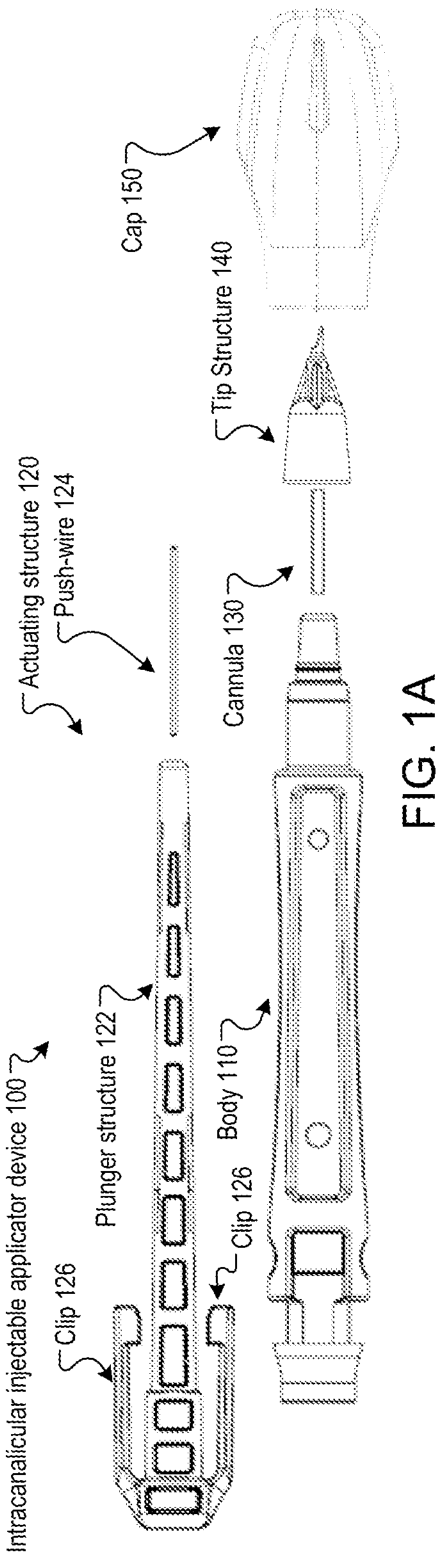
FIGS. 1A-G illustrate intracanalicular injectable applicator devices, according to certain embodiments.

Embodiments described herein are related to intracanalicular depot inserter devices (e.g., intracanalicular injectable applicator devices, punctal dilating applicators for delivering intracanalicular injectables, injector, etc.) used to inject an intracanalicular injectable (e.g., injectable medication, injectable biologic, depot, etc.) into a patient.

Intracanalicular injectables (e.g., polymer based intracanalicular inserts, depots) are used as a therapy for treating a number of conditions present in the eye. The lacrimal punctum is a tiny hole located at the medial corner of both the superior and inferior eyelids. The lacrimal punctum drains tears that are constantly produced by exocrine (lacrimal) glands of the eye. Intracanalicular injectables (e.g., intracanalicular inserts) that are typically cylindrical can be placed into the inferior lacrimal canaliculus through a lacrimal punctum or into the superior lacrimal canaliculus through a lacrimal punctum. Intracanalicular injectables are generally larger in diameter compared to the diameter of the lacrimal punctal opening to assist retention of the intracanalicular injectable. An intracanalicular injectable can be an injectable medication or injectable biologic that is injected by a physician via the lacrimal punctum into a patient. The intracanalicular injectable may be a product that is applicable to the prevention, treatment, or cure of a disease or condition of an eye of a patient.

An additional dilation procedure (e.g., punctal dilation) is used to expand the flexible and delicate punctal tissue located around the lacrimal punctum (e.g., opening of the canaliculus) to allow passage of an intracanalicular injectable. Punctal dilation is an intimidating procedure because punctal dilation is to be performed delicately to prevent damage the surrounding tissue. This additional step of punctal dilation is also cumbersome and time consuming. Many physicians neglect to perform punctal dilation prior to injection (e.g., insertion) of the intracanalicular injectable since punctum diameters range in size significantly between individuals and it is sometimes hard to know when punctal dilation is needed.

During the procedure of injection (e.g., insertion) of an intracanalicular injectable, a hydrophilic polymer-based intracanalicular injectable can absorb moisture from the ocular surface and surrounding tissue, causing the intracanalicular injectable to increase in diameter. This is advantageous for retention of the injectable. However, it presents a challenge to the procedure by limiting the amount of time available to successfully pass the intracanalicular injectable through the lacrimal punctum (e.g., punctal opening).

The small size of an intracanalicular injectable presents an additional challenge because specialized instrumentation that is not standard for surgical procedures are to be used to insert the intracanalicular injectable. Furthermore, the intracanalicular injectable can be damaged if gripped too firmly and potentially dropped if not held firmly enough.

The variable patient dependent nature and use of specialized instrumentation to perform the injection procedure (e.g., insertion procedure) can increase the likelihood of improper intracanalicular injectable placement. The inferior lacrimal canaliculus has two segments: an approximately 2.5 millimeter (mm) long vertical segment connected to an approximately 8 mm long horizontal segment via an angled ampulla. The effectiveness of the intracanalicular injectable and the ability of the intracanalicular injectable to be retained in the canaliculus (e.g., lacrimal canaliculi) depends on initial placement of the intracanalicular injectable during the injection procedure (e.g., insertion procedure). Also, the proximity of the injectable to the punctal opening is important for delivery of an active agent (if present) from the injectable to the tear fluid.

The combination of these factors increases the complexity of the procedure and can lead to a failed injection (e.g., insertion), injured lacrimal tissue, a dropped intracanalicular injectable requiring a second intracanalicular injectable, and a prolonged procedure. The amount of training and skill required to perform the injection procedure (e.g., insertion procedure) can deter physicians from electing to use intracanalicular injectables and can cause frustration when a failure occurs.

The devices, systems, and methods disclosed herein provide an intracanalicular injectable applicator device. The intracanalicular injectable applicator device simplifies and streamlines the injection procedure (e.g., insertion procedure). The intracanalicular injectable applicator device protects the intracanalicular injectable during storage and shipping, easily and safely dilates the lacrimal punctum so that the lacrimal punctum can receive the intracanalicular injectable, and subsequently deploys the intracanalicular injectable into the canaliculus.

An intracanalicular injectable applicator device includes a body forming a cavity and a cannula coupled to a first distal end of the body. The cannula forms a channel that is aligned with the cavity of the body. The cannula is configured to store an intracanalicular injectable in the channel. The intracanalicular injectable applicator device further includes a tip structure coupled to the body. The tip structure is disposed around at least a portion of the cannula. A distal end of the tip structure is configured to dilate a lacrimal punctum by inserting the distal end of the tip structure into the canaliculus via the lacrimal punctum (e.g., and rotating the distal end). The intracanalicular injectable applicator device further includes an actuating structure that may be partially disposed in the cavity of the body and partially disposed in the channel of the cannula. The actuating structure is configured to push the intracanalicular injectable through the channel and the distal end of the tip structure into a canaliculus via a lacrimal punctum while the distal end of the tip structure is inserted into the canaliculus via the lacrimal punctum.

The systems, devices, and methods disclosed herein have advantages over conventional solutions. The intracanalicular injectable applicator device can be used to safely dilate a lacrimal punctal and insert an intracanalicular injectable quicker than conventional solutions which limits the amount of moisture the intracanalicular injectable absorbs and increases success of injection (e.g., insertion). The intracanalicular injectable applicator device avoids damage of the intracanalicular injectable and avoids dropping of the intracanalicular injectable compared to conventional solutions. The intracanalicular injectable applicator device has an increased likelihood of injection (e.g., insertion) and retention of the intracanalicular injectable into the correct location. The intracanalicular injectable applicator device has decreased injuries compared to conventional solutions.

Although certain embodiments of the present disclosure refer to intracanalicular injectables, embodiments of the present disclosure may be used with one or more objects that are to be injected (e.g., inserted, deployed) in the lacrimal punctum and/or canaliculus. In some embodiments, an object may include one or more of an object to be injected (e.g., inserted, deployed) in the canaliculus, an injectable medication, an injectable biologic, an object to deliver medication (e.g., a medicinal drug, therapeutic drug), an object to block the punctum, a plug (e.g., punctum plug, rigid plastic object shaped like an anchor, object with a head to be flush with eyelid, etc.), an injectable (e.g., located just below the lacrimal punctum), an object made of hydrogel, object made of poly (lactic acid) (PLA), object made of poly (lactic-co-glycolic acid) (PLGA), a cylindrical object, bio absorbable object, an object that is to be physically removed, a polymer-based object, an object that expands (e.g., swells to occlude lacrimal punctum), a polymeric object, an elastomeric object, etc.

Although certain embodiments of the present disclosure refer to an intracanalicular injectable applicator device being used to dilate a lacrimal punctum and deploy a single intracanalicular injectable into the canaliculus, embodiments of the present disclosure may be used to deploy multiple intracanalicular injectables (e.g., stacking intracanalicular injectables) into a single canaliculus (e.g., providing a first intracanalicular injectable via a first intracanalicular injectable applicator device into a canaliculus and providing a second intracanalicular injectable via a second intracanalicular injectable applicator device into the same canaliculus, providing a first and a second intracanalicular injectable via the same intracanalicular applicator device into the same canaliculus, etc.).

FIGS. 1A-G illustrate intracanalicular injectable applicator devices 100 (e.g., applicators, plunger-actuated intracanalicular injectable applicator devices, punctal dilating applicators for delivering intracanalicular injectables, injector, etc.), according to certain embodiments. The intracanalicular injectable applicator devices 100 include a body 110, an actuating structure 120, and a cannula 130 (e.g., the intracanalicular injectable is stored in the cannula 130).

The intracanalicular injectable application device 100 can be used to inject (e.g., deploy, insert, etc.) an intracanalicular injectable 160 (e.g., depot) into a patient. The intracanalicular injectable 160 can be an injectable medication or injectable biologic that is injected by a physician via the lacrimal punctum into a patient. The intracanalicular injectable 160 may be a product that is applicable to the prevention, treatment, or cure of a disease or condition of an eye of a patient. In some embodiments, the intracanalicular injectable 160 is a Dextenza® intracanalicular injectable. Intracanalicular injectable 160 may be referred to as an insert or an intracanalicular insert. Intracanalicular injectable application device 100 can be referred to as an intracanalicular insert application device, an injector, an inserter device (e.g., for dilating punctum and delivering intracanalicular injectables), injection device for dilating punctum and delivering intracanalicular injectables, etc. In some embodiments, the intracanalicular injectable 160 includes one or more of travoprost, cyclosporine, or dexamethasone The body 110 forming a cavity (e.g., hollow core, etc.). The cannula 130 is coupled (e.g., attached) to a distal end of the body 110. In some embodiments, the cannula 130 is affixed to the body 110 via adhesion (e.g., glue), insert molding, and/or the like. The cannula 130 forms a channel (e.g., lumen) that is aligned with the cavity of the body 110. The cannula 130 is configured to store an intracanalicular injectable in the channel. In some embodiments, the channel of the cannula 130 is configured to store, protect, and maintain alignment of the intracanalicular injectable. The actuating structure 120 is configured to be partially disposed in the cavity of the body 110 and partially disposed in the channel of the cannula 130. The actuating structure 120 is configured to push the intracanalicular injectable through the channel into a canaliculus via a lacrimal punctum.

The actuating structure 120 can include a plunger structure 122 and a push-wire 124. The plunger structure 122 may be configured to be disposed at least partially in the cavity of the body 110. A first distal end of the plunger structure 122 is configured to receive a force (e.g., a user pressing on the first distal end of the plunger structure 122 with a finger) to cause actuation of the actuating structure 120 (e.g., the plunger structure 122 and push-wire 124). A first distal end of the push-wire 124 is attached to a second distal end of the plunger structure 122. In some embodiments, the second distal end of the plunger structure 122 forms a slot 128 and the first distal end of the push-wire 124 is insert-molded into the slot 128 of the plunger structure 122. A second distal end of the push-wire 124 is disposed in the channel of the cannula 130 prior to the actuation of the actuating structure 120. The push-wire 124 is configured to push the intracanalicular injectable through the channel responsive to the actuation of the actuating structure 122. In some embodiments, the push-wire 124 is a rod. In some embodiments, the push-wire 124 is a metal wire. In some embodiments, the push-wire 124 has a circular perimeter (e.g., is cylindrical) that substantially matches a cylindrical shape of the channel of the cannula 130. In some embodiments, an outer diameter of the push-wire 124 is substantially the same as the inner diameter of the channel of the cannula 130.

The plunger structure 122 may include hooked clips 126 configured to insert into corresponding recesses formed by an outer surface of the body 110 to prevent the plunger structure 122 and the body 110 from separating and to constrain movement of the intracanalicular injectable in the cannula 130.

In some embodiments, a portion of the plunger structure 122 disposed in the cavity of the body has a non-circular perimeter (e.g., oval-shaped, the portion of the plunger structure proximate the hooked clips 126) and a portion of the cavity of the body 110 has a non-circular profile (e.g., oval shaped) that corresponds to the non-circular perimeter of the portion of the plunger structure 122. The actuating structure 120 may be rotated to align the non-circular perimeter of the portion of the plunger structure 122 with the non-circular profile of the portion of the cavity of the body 110 to actuate the actuating structure 120.

In some embodiments, the cavity of the body 110 and an outer profile of the plunger structure 122 are tapered to direct the push-wire 123 into the channel of the cannula 130.

In some embodiments, the intracanalicular injectable applicator device 100 includes a cap 150 that is configured to removably attach to the body 110 proximate the first distal end of the body 110 (e.g., proximate the cannula 130). The cap 150 may form an opening (e.g., vent) to provide ventilation for the intracanalicular injectable.

The intracanalicular injectable applicator device 100 may include a tip structure 140 (e.g., flexible tip, dilator tip) coupled to the body 110. The tip structure 140 is disposed around at least a portion of the cannula 130. A distal end (e.g., tip) of the tip structure 140 is configured to be inserted in the canaliculus via the lacrimal punctum. The actuating structure 120 is configured to push the intracanalicular injectable through the channel of the cannula 130 and the distal end of the tip structure 140 into the canaliculus while the distal end of the tip structure 140 is inserted into the canaliculus via the lacrimal punctum. In some embodiments, the distal end of the tip structure 140 is configured to dilate the lacrimal punctum by inserting the distal end of the tip structure 140 into the canaliculus via the lacrimal punctum and rotating the intracanalicular injectable applicator device 100.

In some embodiments, at least a portion of the distal end (e.g., the tip) of the tip structure 140 has a durometer between 50 and 70. In some embodiments, an opening of the distal end of the tip structure 140 has a diameter that is smaller than an outer diameter of the intracanalicular injectable. In some embodiments, a portion of the distal end of the tip structure 140 includes one or more of a flat tip, a beveled tip, a slit tip, a flat beveled tip, or a round beveled tip. The portion of the distal end of the tip structure 140 is configured to be entirely inserted into the canaliculus via the lacrimal punctum prior to injection (e.g., deployment, insertion) of the intracanalicular injectable into the canaliculus.

In some embodiments, the tip structure 140 does not have a beveled tip. A punctum that is dilated (e.g., via cap 150 or a separate dilating component) or the punctum may have a resting diameter (e.g., above average resting diameter) may receive a tip structure 140 (e.g., that does not have a beveled tip).

In some embodiments, the injectable applicator device 100 includes a collar structure disposed around a portion of the cannula 130 (e.g., instead of a tip structure 140). The collar structure limits depth of insertion of a distal end of the cannula 130 into the canaliculus via the lacrimal punctum. The actuating structure 120 is configured to push the intracanalicular injectable through the channel and into the canaliculus while the distal end of the cannula 130 is inserted into the canaliculus via the lacrimal punctum.

In some embodiments, a system includes the intracanalicular injectable applicator device 100 and an intracanalicular injectable (e.g., loaded in the channel of the cannula 130 of the intracanalicular injectable applicator device 100). In some embodiments, a kit includes an enclosure to house components (e.g., see FIG. 12I). The components may include an intracanalicular injectable applicator device 100 and an intracanalicular injectable (e.g., intracanalicular injectable loaded into the intracanalicular injectable applicator device 100 in the locked position and with a cap 150 placed on the body 110 in the kit, intracanalicular injectable separate from the intracanalicular injectable applicator device 100 in the kit). The enclosure may be a foil pouch. The components in the kit may include a desiccant.

The intracanalicular injectable applicator device 100 may be economical to be accurately injection molded with thermoplastics, thermosets, and/or machined metal components.

In some embodiments, the intracanalicular injectable applicator device 100 does not have adhesives. The intracanalicular injectable applicator device 100 may be designed in a manner that eliminates the need for adhesives that could contribute to mechanical failures and moisture in the packaging. The cannula 130 (e.g., texturized hypodermic cannula) may be insert-molded to the body 110 (e.g., plastic handle).

In some embodiments, the intracanalicular injectable is cylindrical in shape and is stored within the lumen (e.g., channel) of the cannula 130 for protection during storage and to maintain alignment. Also, within the lumen of the cannula 130 is a short length of the push-wire 124 positioned behind the intracanalicular injectable. The push-wire 124 may constrain one end of the intracanalicular injectable (e.g., cylindrical injectable) and may prevent the intracanalicular injectable from moving in the medial direction. The push-wire 124 may be insert-molded onto the plunger structure 122 without the use of adhesives and may at least partially rest within the cavity of the body 110 (e.g., within the hollow core of the handle). The plunger structure 122 may have hooked clips 126 that are constrained by indents in the body 110 to prevent the plunger structure 122 and body 110 (e.g., body assembly) from coming apart. This may further constrain the intracanalicular injectable from migrating in the medial direction and may maintain positioning of the intracanalicular injectable throughout storage.

The tip structure 140 may be a flexible tip that surrounds the cannula 130 (e.g., hypodermic cannula) that contains the intracanalicular injectable. The tip structure 140 has a distal end (e.g., flexible tip) that has an inner diameter that is smaller than the diameter of an intracanalicular injectable which prevents the intracanalicular injectable from migrating in the distal direction during movement of the intracanalicular injectable applicator device 100 (e.g., during worst case shipping conditions). The material properties and flexibility of the distal end (e.g., flexible tip) of the tip structure 140 may allow passage of the intracanalicular injectable when a threshold force (e.g., a significant force) is applied.

The tip structure 140 may form an annular recess (e.g., formed by an inner surface of the tip structure 140) that snaps onto a corresponding annular protrusion (e.g., formed by the outer surface of the body 110) on the body 110 that secures the tip structure 140 (e.g., flexible tip) in place. This may simplify the assembly procedure and may enhance consistent repeatability.

In some embodiments, the cap 150 (e.g., protective cap) friction fits over the body 110. A light press fit may be achieved via ridges lining an inner diameter of the cap 150 in the longitudinal direction. The ridges may create an inner diameter that is smaller than the outer diameter of the body 110 (e.g., the ridges may slot onto the outer diameter of the body).

The inner circular core (e.g., cavity) of the body 110 and the circular shaft of the plunger structure 122 may have a taper to facilitate assembly. As the plunger structure 122 gets slotted into the body 110, the taper profile directs the push-wire 124 into the cannula 130. The base of the inner core (e.g., cavity) of the body 110 may form a chamfer to funnel the push-wire 124 into the cannula 130 to prevent jamming during assembling.

The plunger structure 122 and the body 110 may form a "lock and key" locking mechanism to prevent unintentional deployment of the intracanalicular injectable during shipping and handling. The body 110 may be cylindrically tubular and may form a non-circular (e.g., oval-shaped) slot (e.g., a portion of the cavity may have a non-circular profile) that extends a certain distance into the cylindrical core of the body 110. The plunger structure 122 may have a corresponding non-circular (e.g., oval-shaped) perimeter (e.g., extrusion) that extends a distance down the cylindrical shaft of the plunger structure 122. The non-circular perimeter on the plunger structure 122 is to line up with the non-circular profile of the body 110 in order to travel in the axial direction. If the non-circular perimeter and the non-circular profile (e.g., oval-shaped features) are not aligned, the maximum width of the non-circular perimeter of the plunger structure 122 (e.g., oval extrusion of the plunger structure 122) interferes with the minimum width of the non-circular profile of the body 110 (e.g., the ovular slot of the body 110).

In addition to the "lock and key" mechanism preventing unintentional forward actuation in the "locked position" (e.g., when the non-circular perimeter of the plunger structure 122 is not aligned with the non-circular profile of the body 110), the intracanalicular injectable applicator device 100 may have another feature that prevents unintentional rotation of the plunger structure 122. The plunger structure 122 may include two clips 126 that are a set distance apart (e.g., on opposite sides of the plunger structure 122). The body 110 has a square profile where the clips 126 rest on the body 110. The square profile may be designed to prevent the plunger structure 122 from rotating until a threshold force (e.g., a significant force) is applied to rotate the plunger structure 122). The width of the body in the location of the square profile may match the resting clip separation distance. Responsive to the plunger structure 122 being rotated 45 degrees, the clips 126 of the plunger structure 122 may flex to overcome the diagonal distance of the square profile of the body 110. The clips 126 of the plunger structure 122 may provide a spring force that prevents rotation as a result of certain movements (e.g., worse case shipping conditions). The rotation force can be achieved with one finger.

The width of the square feature when the plunger structure 122 is positioned in the "unlocked position" may be greater (e.g., slightly greater) than the resting width of the clips 126 of the plunger structure 122 which may cause the clips 126 to flex and create friction to prevent the plunger from moving in the "unlocked position" until a threshold force (e.g., significant force) is applied. The interface between the flexing clips 126 of the plunger structure 122 and the square feature (e.g., square profile) of the body 110 may provide physical feedback to the end user when the intracanalicular injectable procedure is being performed.

The cap 150 may have a cutout window that allows enhanced ventilation for the tip structure 140 (e.g., flexible tip) and the intracanalicular injectable (e.g., polymer-based intracanalicular injectable). In some embodiments, the intracanalicular injectable and plastic material (e.g., of the tip structure 140) are to have removal of moisture via inert nitrogen conditioning and a cutout in the cap 150 (e.g., protective cap) may enhance the rate of latent moisture removal from the internally-stored intracanalicular injectable (e.g., polymer-based insert) and surrounding materials. The plastic material (e.g., of the tip structure 140) may exhibit low $H_2O$ adhesion and cohesion properties.

The intracanalicular injectable applicator device 100 may be configured to dilate the lacrimal punctum to a threshold diameter to receive the intracanalicular injectable and to subsequently inject (e.g., deploy, insert) the intracanalicular injectable into the vertical canaliculus through one streamlined procedure without using additional operations. One or more alert indicators may be incorporated into the intracanalicular injectable applicator device 100 to provide one or more alerts to the user.

The distal end (e.g., tubular flexible tip) of the tip structure 140 may be beveled to allow the very tip of the bevel to come to an ovular point with dimensions that allow use on puncta of different sizes.

The distal end (e.g., tip) of the tip structure 140 may be tube-shaped to allow passage of an intracanalicular injectable and may have a beveled tip so that only one wall is used to initially find the punctal opening. This permits a larger wall thickness resulting in a more rigid tool to perform dilation to be used on puncta of different sizes.

The distal end (e.g., tip) of the tip structure 140 may have a bevel that has a rounded tip and an ovular profile which may prevent trauma and enhance ability of the user to perform the initial dilation of the punctum. The ovular tip profile when inserted into the circular punctal opening initially elongates the tissue on one plane. The ovular tip can be rotated to expand the entire circumference of the punctum. This may reduce the rate of dilation and allow successful use on patients with small punctal openings.

The tapered profile of the beveled tip of the distal end of the tip structure 140 may enable the tip structure 140 to progressively dilate the punctal opening to a threshold diameter (e.g., a diameter that is large enough to receive the intracanalicular injectable). A slow and delicate rate of dilation is used to not cause trauma to fibroelastic tissue that surrounds the punctal opening. The angle of the bevel of the distal end of the tip structure 140 may optimize the rate of dilation as the bevel is slotted into the canaliculus.

The flexibility and tubular structure of the distal end (e.g., dilating tip) of the tip structure 140 prevents aggressive dilation. The distal end (e.g., tip) of the tip structure 140 can collapse and conform to the smaller canaliculi profile when the distal end is initially inserted and then slowly expand to the original shape of the distal end while exhibiting an outward force which causes the canalicular tissue to gradually expand.

Once the entire bevel of the distal end (e.g., tip) of the tip structure 140 is slotted inside the canaliculus, the outer diameter of the tip structure 140 (e.g., dilating tip) abruptly increases to a diameter that prevents further insertion and over dilation (e.g., the tip structure 140 has a distal end that is configured to enter the canaliculus and the distal end is adjacent to a portion of the tip structure 140 that has a greater diameter than the distal end and is not configured to enter the canaliculus). Over dilating the diameter of the punctal opening or canaliculus could damage the fibroelastic punctal tissue and/or result in an orifice that is too large to properly retain the intracanalicular injectable.

Once a threshold dilation (e.g., adequate dilation) is achieved, the intracanalicular injectable applicator device 100 can be used in a syringe-like manner to transmit an axial load along the push-wire 124 to eject the intracanalicular injectable through the lumen of the tip structure 140 (e.g., flexible tip). Having a portion of the push-wire 124 rest within the cannula 130 prior to actuation additional maintains the alignment of the push-wire 124 and prevents the possibility of a misfire. The inside wall of the cannula 130 (e.g., hypodermic cannula) prevents wire deflection and maintains a linear axial force vector that pushes the intracanalicular injectable into the canaliculus.

A user (e.g., based on the average size of an adult hand) can unlock and actuate the plunger with the index finger. The intracanalicular injectable applicator device 100 can remain in and function with one hand through the entire duration of the insertion procedure (e.g., one hand insertion).

The non-circular (e.g., oval-shaped) "lock and key" locking mechanism" may provide ambidextrous functionality. Utilizing a non-circular (e.g., oval-shaped) can accomplish this by allowing the plunger structure 122 and body 110 to "unlock" and align when rotated 90 degrees clockwise and when rotated 90 degrees counterclockwise.

The abrupt increase in outer diameter of the tip structure 140 (e.g., dilating tip) acts as a physical barrier and dictates the position of the tip in the canaliculus prior to injection (e.g., deployment, insertion) of the intracanalicular injectable. The ability to accurately position the distal end (e.g., tip) of the tip structure 140 in the canaliculus may provide an accurate and consistent placement of the intracanalicular injectable (e.g., polymer-based insert) regardless of human factors.

The injection (e.g., deployment, insertion) depth of the intracanalicular injectable may be controlled by the depth of the non-circular portion of the cavity (e.g., oval-shaped cutout) internal to the body 110. Once the non-circular portion (e.g., oval-shaped portion) of the cavity converts to a circular portion, the portion of the plunger structure 122 that has a non-circular (e.g., ovular shaped) perimeter can no longer proceed forward.

The fixed stroke length of the plunger structure 122 and push-wire 124 (e.g., plunger and push-wire assembly) in combination with the distal end (e.g., tip) insertion barrier of the tip structure 140 cause the intracanalicular injectable to be consistently injected (e.g., deployed, inserted) to a predetermined depth. These features that dictate injection (e.g., deployment, insertion) depth may be selected to deliver the intracanalicular injectable to the vertical segment of the lower lacrimal canaliculus.

A shorter push-wire 124 can be used to deliver the intracanalicular injectable a maximum depth of 1 millimeter (mm) below the punctal opening so that the intracanalicular injectable resides just above the angled ampulla in the vertical segment of the lower lacrimal canaliculus. The short injection (e.g., deployment, insertion) depth can be provided in part by the beveled distal end (e.g., beveled tip) of the tip structure 140) which allows the intracanalicular injectable to be released at a shorter distance.

To place the intracanalicular injectable in the horizontal region of the lower lacrimal canaliculus, the length of the push-wire 124 can be increased to push the intracanalicular injectable past the ampulla. The flexibility of the distal end of the tip structure 140 (e.g., dilating tip) can conform to the lacrimal anatomy and can guide the intracanalicular injectable past the curved ampulla.

In some embodiments, the intracanalicular injectable applicator device 100 has audible and/or physical feedback indicating injection (e.g., deployment, insertion) of the intracanalicular injectable. The audible and/or physical feedback may result from how the clips 126 of the plunger structure 122 interface with the body 110 once the plunger structure 122 reaches a final "deployed position," "injected position," or "inserted position." Once the plunger structure 122 reaches the deployed position, the clips 126 of the plunger structure 122 snap into a recess in the body 110 which produces an audible click. Having the plunger structure 122 click into place in the deployed position also secures the push-wire 124 in the exposed position (e.g., extended position of the push-wire 124) and allows the user to further push the intracanalicular injectable into place (e.g., if applicable) without the push-wire 124 retracting. The clips 126 of the plunger structure 122 snapping into recesses in the body 110 may be physically felt through the mechanical vibration of the intracanalicular injectable applicator device 100 when the clips 126 snap into the recesses.

The intracanalicular injectable applicator device 100 may include a visual feedback indicator (e.g., in addition to or instead of the audible and/or physical feedback). The plunger structure 122 may have indicators (e.g., red and green markings printed on the plunger). The actuating structure 120 may be the only moving component in the intracanalicular injectable applicator device 100. The indicators may be viewed through cutout holes that peer into the cavity of the body 110. The position of a first indicator (e.g., red marking) when transitioning to a second indicator (e.g., green marking) may align when the intracanalicular injectable is fully injected (e.g., deployed, inserted).

The dimensions of the push-wire 124, cannula 130 (e.g., hypodermic cannula), and tip structure 140 (e.g., flexible tip) can be adjusted to accommodate intracanalicular injectables of different sizes. The intracanalicular injectable applicator device 100 streamlines the insertion procedure and reduces complexity. The amount of time to perform the insertion proceed can be reduced to mitigate the likelihood of an unsuccessful insertion by preventing the intracanalicular injectable from expanding prior to placement in the canaliculus.

The design and composition of the intracanalicular injectable applicator device 100 may include a cannula 130 (e.g., hypodermic cannula) that is insert-molded onto a body 110 (e.g., cylindrically tubular body) without adhesive. The cannula 130 may constrain the intracanalicular injectable from lateral movement. The push-wire 124 may be insert-molded onto the plunger structure 122 without adhesive. The actuating structure 120 (e.g., push-wire 124 and plunger structure 122 subassembly) may be assembled within the cavity (e.g., core) of the body 110). The push-wire 124 may constrain the intracanalicular injectable from proximal movement. The plunger structure 122 may have hooked clips 126 that interface with the body 110 to prevent the plunger structure 122 and body 110 (e.g., plunger and body assembly) from coming apart. The tip structure 140 (e.g., flexible tip) may surround the cannula 130 (e.g., hypodermic cannula) and may constrain distal movement of the intracanalicular injectable. The tip structure 140 may have material properties and flexibility that allows passage of the intracanalicular injectable when a threshold force is applied. The tip structure 140 may have an annular recess that snaps onto a corresponding annular protrusion on the body 110 to secure the tip structure 140 in place and which may reduce assembly time. A cap 150 (e.g., protective cap) may friction fit over the body 110. The friction fit may be created by ridges internal to the cap. A portion of the push-wire 124 may rest within the cannula 130 prior to actuation to maintain alignment of the push-wire 124 and to prevent possibility of a misfire of the push-wire 124. The body 110 may have a cavity (e.g., inner circular core) and the shaft of the plunger structure 122 may be tapered to aid alignment of the push-wire 124 during assembly. A chamber at the base of the cavity (e.g., inner core) of the body 110 may funnel the push-wire 124 into the cannula 130.

The intracanalicular injectable applicator device 100 may prevent unintentional deployment of the intracanalicular injectable (e.g., via a locking feature that constrains the plunger structure 122). The body (e.g., cylindrically tubular body) may include a non-circular (e.g., oval-shaped) slot that extends into the cylindrical core. A plunger structure 122 with a substantially identical non-circular (e.g., oval-shaped) extrusion extends down the cylindrical shaft of the plunger structure 122. The non-circular perimeter of the plunger structure 122 is to line up with the non-circular profile (e.g., oval slot) of the body 110 to travel in the distal direction. A deployment depth or stroke depth may be directly dependent on the depth of the non-circular portion (e.g. ovular-shaped cutout) internal to the body 110 that is also used as a locking feature. A plunger structure 122 can be rotated clockwise and counterclockwise to align with the body 110 for deployment. Flexible clips 126 of the plunger structure 122 and a square profile of the body 110 may interface with each other to prevent rotation of the plunger structure 122 until a threshold force is applied (e.g., via one finger). Clips 126 of the plunger structure 122 may provide a spring force that can be applied (e.g., countered, overcome) with one finger. The flexible clips 126 of the plunger structure 122 and the square profile of the body 110 may interface to provide physical feedback in the form of resistance when the plunger structure 122 is actuated.

A cap 150 (e.g., protective cap) may have cutout windows that allow a higher rate of $H_2O$ diffusion of the internally stored polymer-based intracanalicular injectable and components. To administer hygroscopic intracanalicular injectables that are unstable in the presence of $H_2O$, the plastic material used to fabricate the intracanalicular injectable applicator device 100 may have low moisture cohesion and adhesion properties. Mitigating $H_2O$ exposure within packaging of the intracanalicular injectable may help maintain the integrity of the intracanalicular injectable in storage. In some embodiments, an intracanalicular injectable applicator device 100 (e.g., that is loaded with an intracanalicular injectable) may be stored in a desiccant-lined foil pouch that is configured to remove internal moisture and prevent moisture ingress. The intracanalicular injectable applicator device 100 loaded with an intracanalicular injectable may be stored in a foil pouch with a desiccant packet.

The distal end of the tip structure 140 may be a tubular flexible tip that is beveled to allow the very tip of the bevel to come to an ovular point with a perimeter (e.g., circumference) that can slot into puncta of different sizes. The bevel tip may be rounded at the end to prevent trauma. The bevel may allow a greater wall thickness for increased tip rigidity while maintaining a profile that is small enough to dilate a small punctal opening. The ovular-shaped bevel tip profile may reduce rate of initial dilation as the tip first elongates the punctal opening in one direction and allows the user to gradually dilate in all direction when rotated. This permits use on patients with a small punctal opening. The bevel may be tapered to allow a steady and progressive rate of punctal dilation without causing trauma to punctal tissue. The flexible tubular tip is able to collapse when initially inserted into the canaliculus and gradually expand, resulting in a slower rate of dilation. The tip structure 140 (e.g., flexible dilating tip) may have an outer diameter that abruptly increases to prevent further insertion and over-dilation.

The intracanalicular injectable applicator device 100 may be used in a syringe-like manner to transmit an axial load along a push-wire 124 to eject the intracanalicular injectable through the lumen of the tip structure 140 (e.g., flexible dilating tip). The intracanalicular injectable applicator device 100 may store an intracanalicular injectable, dilate the punctum, and subsequently inject (e.g., deploy, insert) the intracanalicular injectable and can be completely operated with one hand. The intracanalicular injectable applicator device 100 can be operated with completely ambidextrous functionality.

The intracanalicular injectable applicator device 100 may consistently inject (e.g., deploy, insert) an intracanalicular injectable to the vertical segment of the canaliculus. The beveled tip allows the intracanalicular injectable to be released from the beveled tip at a shorter distance. The intracanalicular injectable applicator device 100 may inject (e.g., deploy, etc.) an intracanalicular injectable past the vertical canaliculus and ampulla so that the intracanalicular injectable resides in the horizontal segment of the lacrimal canaliculus. The tip structure 140 can help guide the deployment of the intracanalicular injectable past the curved ampulla.

The intracanalicular injectable applicator device 100 may have a feedback feature that can be audibly and/or physically detected once the intracanalicular injectable is fully deployed. The clips 126 of the plunger structure 122 may snap into a recess in the body 110 once the plunger structure 122 is fully deployed. The dimensions of the body 110 and the clips 126 of the plunger structure 122 may snap in a manner that can be felt (e.g., as a vibration) and heard as an audible click. Clips 126 of the plunger structure 122 that are held in the recesses of the body 110 may only be moved by a threshold force (e.g., cannot be moved without the application of significant force).

The intracanalicular injectable applicator device 100 may have a visual cue feature that can be visually detected once the intracanalicular injectable is fully deployed. In some embodiments, markers on the plunger structure 122 (e.g., a red and green marking printed on the plunger structure 122) can be viewed through cutout holes that peer into the cavity of the body 110. A first marker (e.g., green marker) can only be seen through the cutout holes when the intracanalicular injectable is fully deployed. A second marker (e.g., red marker) may be visible only when the intracanalicular injectable is pre-loaded into the intracanalicular injectable applicator device 100 (e.g., and the plunger structure 122 has not been actuated).

In some embodiments, the actuation structure 120 includes a plunger structure 122 coupled to a push-wire 124. In some embodiments, the actuation structure 120 includes a slider structure coupled to a push-wire 124. An intracanalicular injectable applicator device 100 that includes a plunger structure 122 may be used in a syringe-like manner to transmit an axial load through a push-wire 124 to inject (e.g., deploy, insert) the intracanalicular injectable. The force is applied to a plunger structure 122 on the distal end of the intracanalicular injectable applicator device 100. For an intracanalicular injectable applicator device 100 that includes a slider structure, the slider structure travels laterally along the body to transmit the axial load.

In some embodiments, the intracanalicular injectable applicator device 100 includes a cannula 130 that is beveled. The cannula 130 may be a hypodermic metal cannula that is custom-machined to have a blunt tip and tapered bevel. The blunt tip prevents the intracanalicular injectable applicator device 100 from perforating the lacrimal tissue and allows the intracanalicular injectable applicator device 100 to find the punctal opening to begin dilation. The tapered bevel may be configured to gradually dilate the punctum as the tapered bevel is driven into the canaliculus. The intracanalicular injectable is stored within the lumen of the cannula 130 and can be injected (e.g., deployed, inserted) via the actuation structure 120 (e.g., plunger structure or slider structure). The bevel may expose an adequate amount of the surface of the intracanalicular injectable to the canalicular tissue so that when the cannula 130 is removed, the intracanalicular injectable is held in place by the friction force between the intracanalicular injectable and canalicular tissue. This prevents the intracanalicular injectable from getting inadvertently removed with the intracanalicular injectable applicator device 100.

A collar (e.g., metal collar) may be provided around the cannula 130 to prevent over-insertion of the cannula 130 into the canaliculus.

In some embodiments, the intracanalicular injectable applicator device 100 includes a tip structure 140 that is flexible. The tip structure 140 may be used similarly as a cannula 130 that is beveled. The softness of the tip of the tip structure 140 may mitigate the risk of lacrimal tissue perforation, thus increasing safety of the intracanalicular injectable applicator device 100. The lumen of the tip structure 140 (e.g., flexible tip) may be undersized to retain the intracanalicular injectable during storage and the flexible nature of the tip material allows the intracanalicular injectable to pass through when the actuation force is applied. The tip material is rigid enough to adequately dilate the punctum.

Either a cannula 130 that is beveled or a tip structure 140 that is flexible may be used. Both may provide for punctum dilation (e.g., increase the diameter of the punctum to be large enough to receive an intracanalicular injectable) and to allow passage and deposition of an intracanalicular injectable in the canaliculus.

One or more components of the intracanalicular injectable applicator device 100 may be three-dimensionally (3D) printed. The intracanalicular injectable applicator device 100 may be used for insertion of intracanalicular injectables (e.g., polymer inserts) into the mammalian lacrimal canaliculus.

In some embodiments, the intracanalicular injectable applicator device 100 stores multiple intracanalicular injectables and is used to insert multiple intracanalicular injectables in multiple canaliculi. In some embodiments, the intracanalicular injectable applicator device 100 is used to apply one or more products (e.g., liquid, solid, medicine, etc.) to the lacrimal punctum and/or canaliculus. In some embodiments, the intracanalicular injectable applicator device 100 is used to insert an intracanalicular injectable that includes medication (e.g., to apply medication). In some embodiments, the intracanalicular injectable applicator device 100 is used to insert an intracanalicular injectable that does not include medication (e.g., used just to occlude).

Figure 1B:
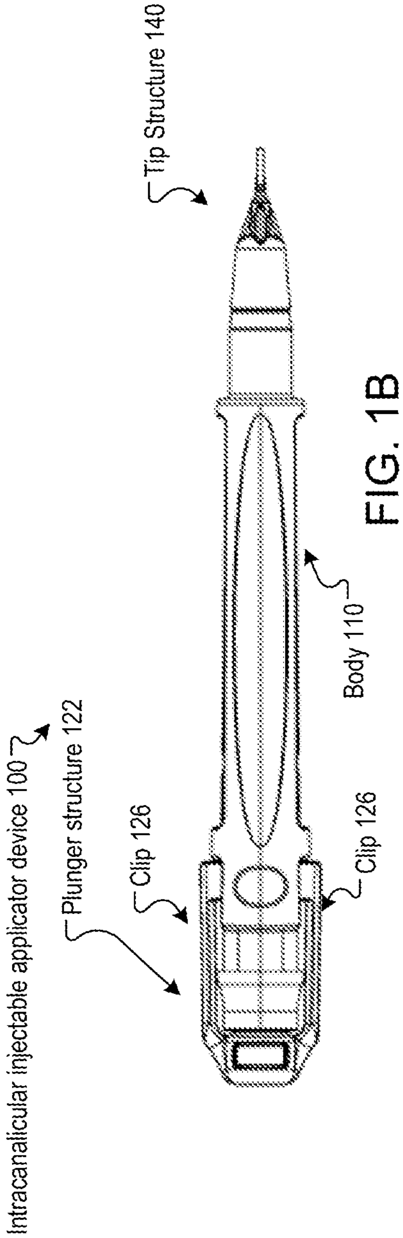
Figure 1C:
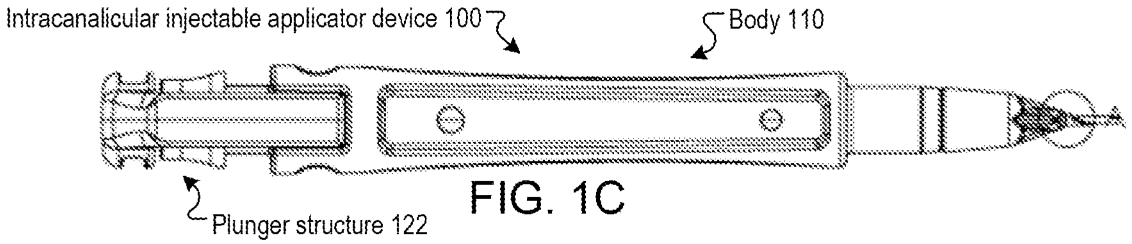
Figure 1D:
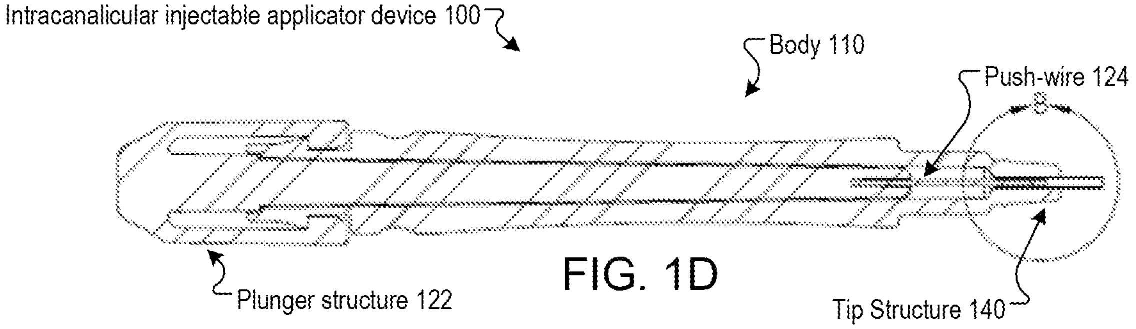
Figure 1E:
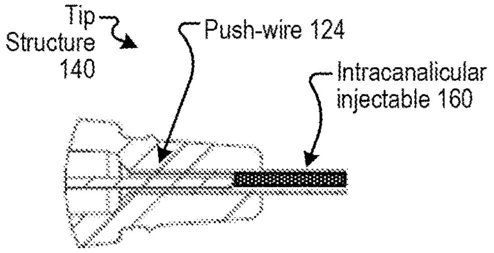
Figure 1F:
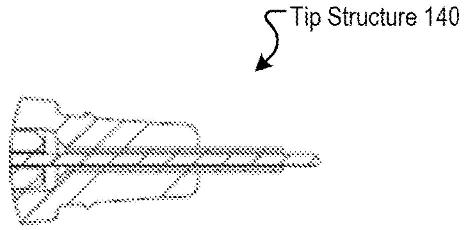
Figure 1G:
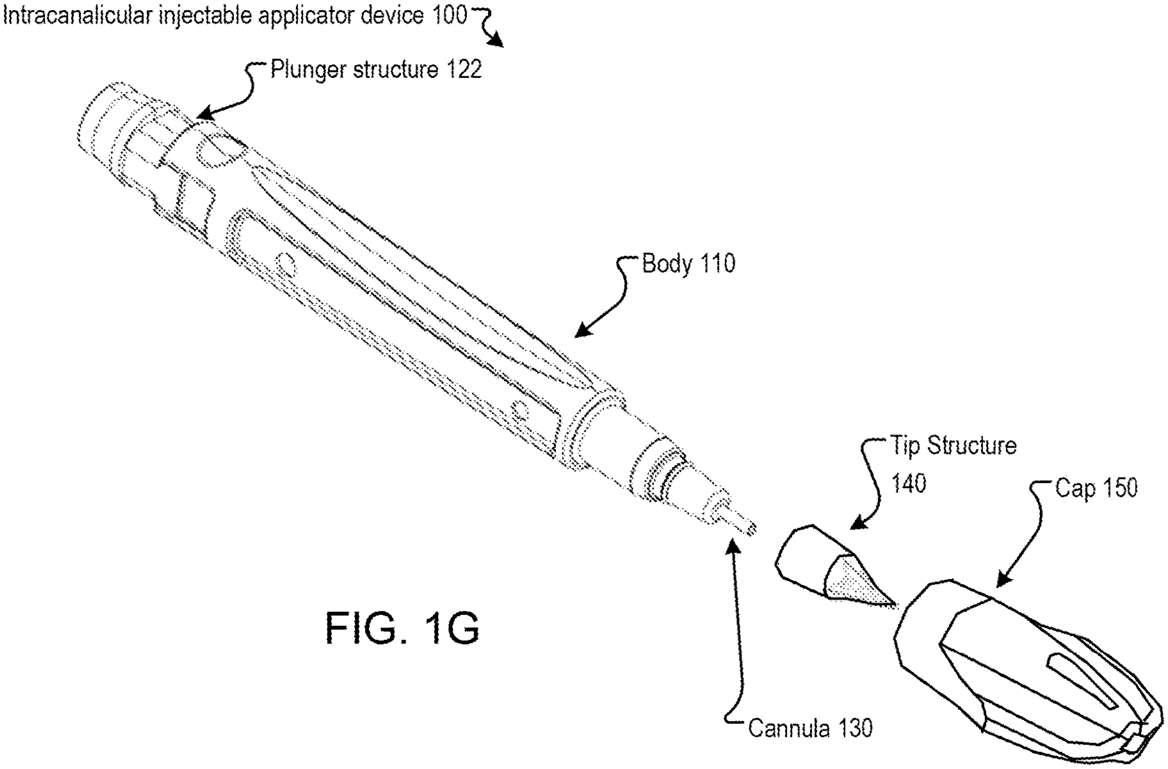

FIG. 1A illustrates an exploded view of an intracanalicular injectable applicator device 100 including a body 110, an actuating structure 120 (e.g., plunger structure 122 and push-wire 124), a cannula 130, a tip structure 140, and a cap 150. FIG. 1B illustrates an assembled intracanalicular injectable applicator device 100 (e.g., without a cap 150) including a body 110, a plunger structure 122, and a tip structure 140. FIG. 1C illustrates an assembled intracanalicular injectable applicator device 100 (e.g., without a cap 150) that has been rotated 90 degrees compared to FIG. 1B. FIG. C illustrates a side view of the intracanalicular injectable applicator device 100 (e.g., without a cap 150). FIG. 1D illustrates a cross-sectional view of an intracanalicular injectable applicator device 100 (e.g., without a cap 150). FIG. 1E illustrates a cross-sectional view of a tip structure 140 of an intracanalicular injectable applicator device 100 that has an intracanalicular injectable 160 (e.g., Dextenza® intracanalicular injectable) that has not been deployed (e.g., the push-wire 124 is in an undeployed position). FIG. 1E illustrates a cross-sectional view of a tip structure 140 of an intracanalicular injectable applicator device 100 (e.g., the intracanalicular injectable has been deployed, the push-wire 124 is in a deployed position). FIG. 1G illustrates a perspective view of an intracanalicular injectable applicator device 100 that has a tip structure 140 and cap 150 removed.

In some embodiments, the total length of the intracanalicular injectable applicator device 100 (e.g., without the cap 150) is about 62 to 80 millimeters (mm). In some embodiments, the tip structure 140 is about 12 mm long. In some embodiments, the distal end (e.g., tip) of the tip structure 140 is about 1 to 5 mm long. In some embodiments, the width of the plunger structure 122 (e.g., outer surface of one clip 126 to outer surface of opposite clip 126) is about 9 mm. A maximum width of the body 110 is about 6 mm. A length of a central portion (e.g., gripping portion) of the body 110 is about 37 mm. A length of a portion of the intracanalicular injectable applicator device 100 between the central portion of the body 110 and the distal end (e.g., end of the tip) of the tip structure 140 is about 19 mm. In some embodiments, the cannula 130 is about 8 to 9 mm long.

In some embodiments, the cannula 130 is affixed to the body 110 via insert molding with about 1 pound (lb) minimum tensile strength. In some embodiments, the push-wire 124 is affixed to the plunger structure 122 via insert molding with about 1 lb min. tensile strength. In some embodiments, the actuating structure 120 (e.g., plunger structure 122 and push-wire 124) are placed in the body 110 and deploy forward without obstruction. In some embodiments, the applicator assembly (e.g., body 110, actuating structure 120, and cannula 130 assembled together), the tip structure 140, and the cap 150 are separately packaged.

Figure 2A:
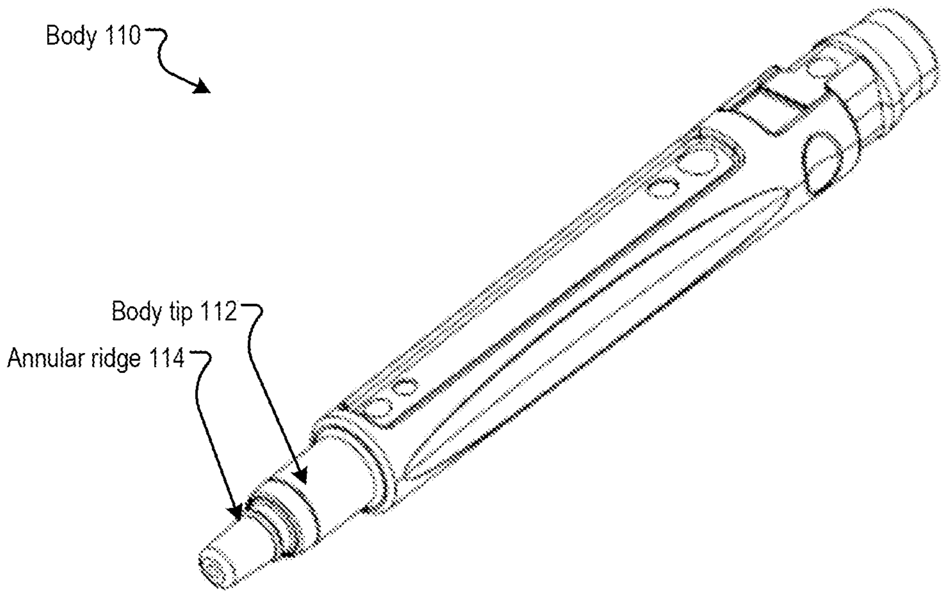
FIGS. 2A-F illustrate a body of an intracanalicular injectable applicator device, according to certain embodiments.
Figure 2B:
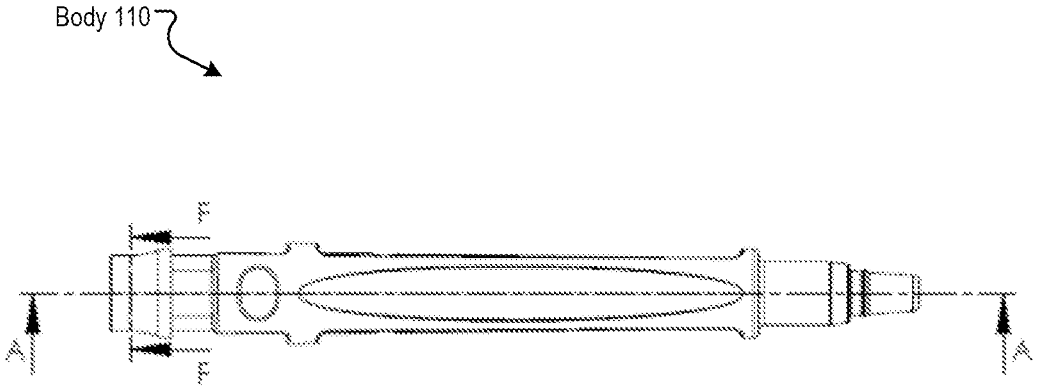
Figure 2C:
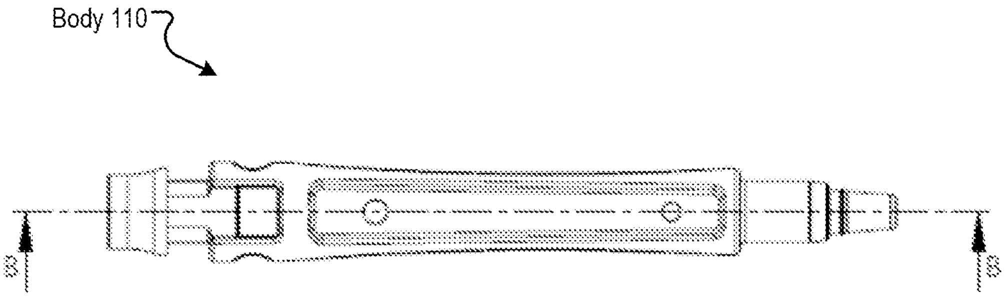
Figure 2D:
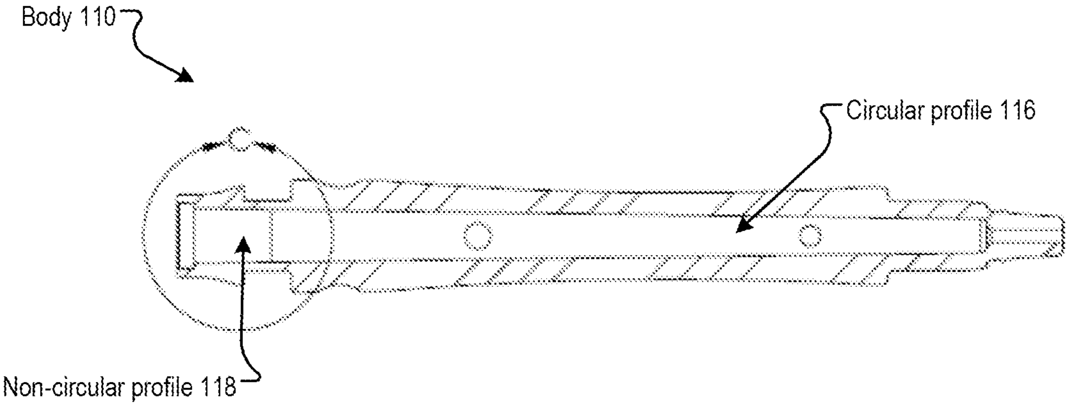
Figure 2E:
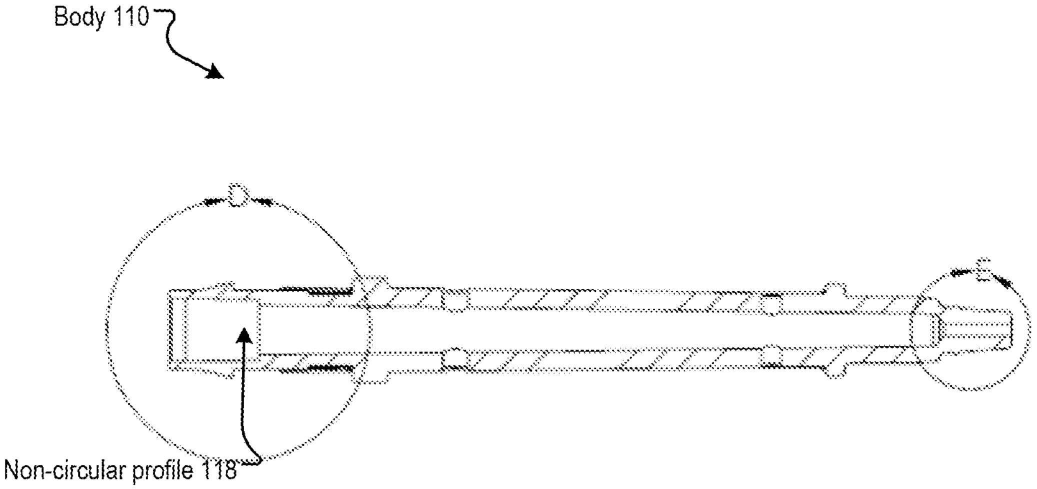
Figure 2F:
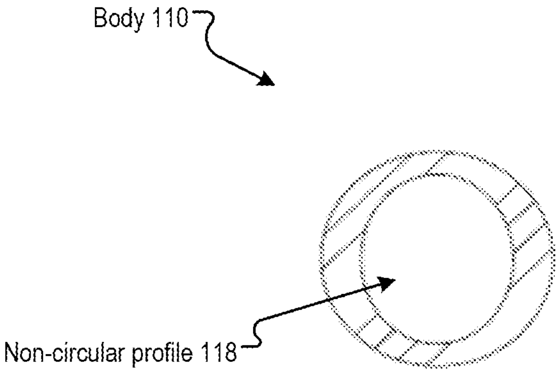

FIGS. 2A-F illustrates a body 110 of an intracanalicular injectable applicator device 100, according to certain embodiments. FIG. 2A illustrates a perspective view of the body 110. FIG. 2B illustrates a first side view of the body 110. FIG. 2B illustrates a first side view of the body 110. FIG. 2C illustrates a second side view (e.g., rotated 90 degrees compared to FIG. 2B) of the body 110. FIG. 2D illustrates a first cross-sectional view of the body 110. FIG. 2E illustrates a second cross-sectional view (e.g., rotated 90 degrees compared to FIG. 2D) of the body 110. FIG. 2F illustrates a cross-sectional view of a non-circular portion of body 110.

In some embodiments, the body 110 has a body tip 112 and an annular ridge 114. In some embodiments, the body 110 does not have a grease or mold release. In some embodiments, the cap 150 lightly press fits over the body tip 112 (e.g., over about 5 mm body tip 112). In some embodiments, the tip structure 140 is held in position by a protrusion (e.g., about 0.15 mm bump).

The body 110 may form a cavity that has a first portion with a circular profile 116 and a second portion with a non-circular (e.g., oval-shaped) profile 118. The plunger structure 122 may be rotated 90 degrees to align with the non-circular profile 118 to be actuated to push the intracanalicular injectable out of the intracanalicular injectable applicator device 100.

FIGS. 3A-F illustrate actuating structures 120 of intracanalicular injectable applicator devices 100, according to certain embodiments.

Figure 3A:
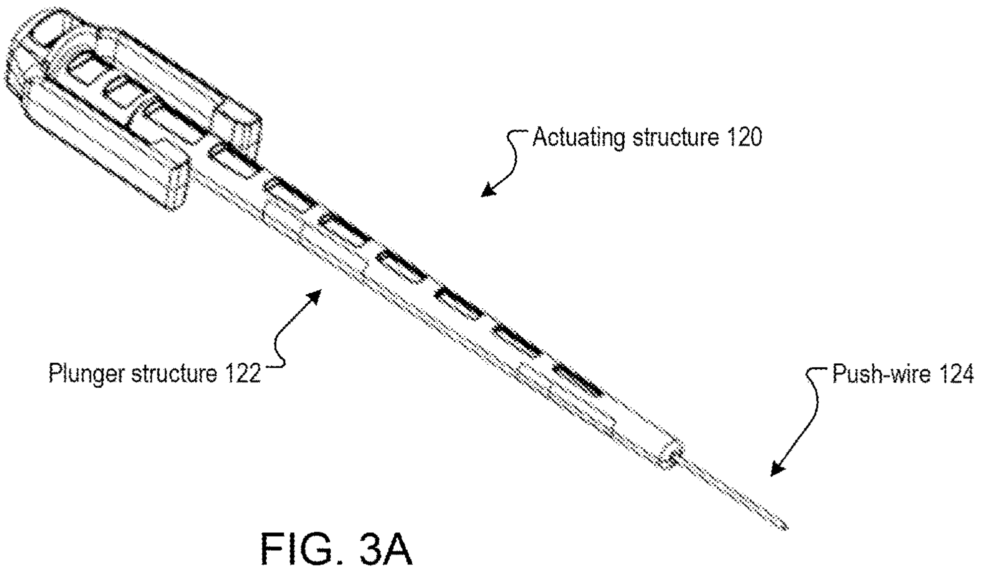
FIGS. 3A-G illustrate actuating structures of intracanalicular injectable applicator devices, according to certain embodiments.
Figure 3B:
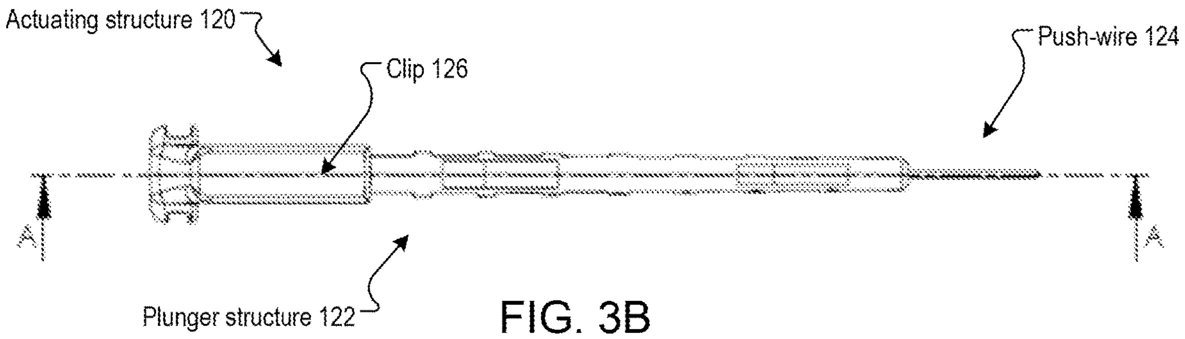
Figure 3C:
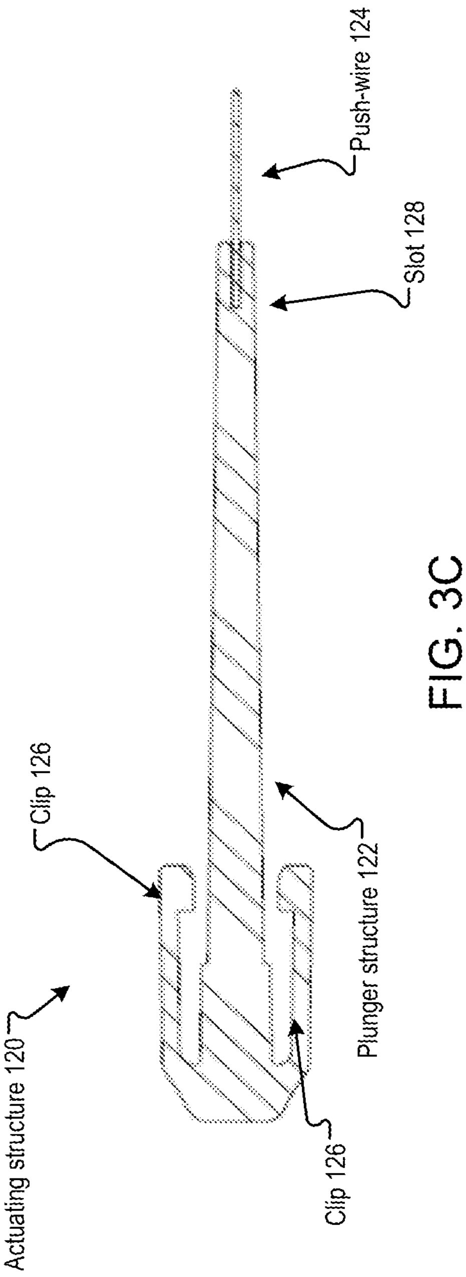
Figure 3E:
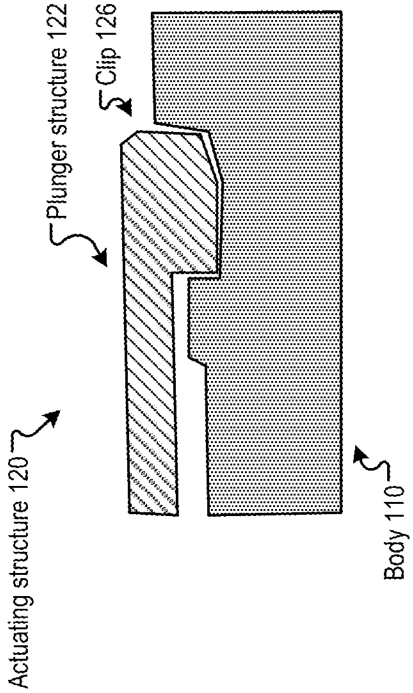
Figure 3D:
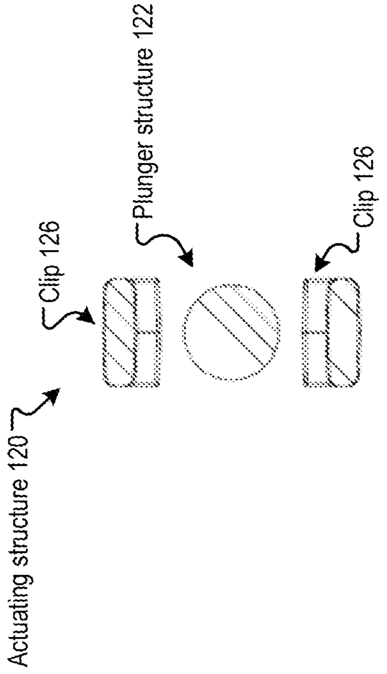

FIGS. 3A-D illustrate an actuating structure 120 that includes a plunger structure 122. FIG. 3A is a perspective view of the actuating structure 120. FIG. 3B is a side view of the actuating structure 120. FIG. 3C is a first cross-sectional view of the actuating structure 120. FIG. 3D is a second cross-sectional view of the actuating structure 120.

The plunger structure 122 may not have a grease or mold release. The push-wire 124 may be adhered (e.g., glued), insert molded, and/or the like into a slot of the plunger structure 122. A portion of the plunger structure 122 proximate the clips 126 may have a non-circular perimeter that substantially matches a non-circular profile of a portion of the cavity of the body 110. To actuate the intracanalicular injectable applicator device 100, the plunger structure 122 is to be rotated so that the portion of the plunger structure 122 with a non-circular perimeter is aligned with the non-circular profile of a portion of the cavity of the body 110.

Both distal ends of the push-wire 124 may be cut, rounded, and deburred. In some embodiments, the push-wire 124 may undergo a passivation operation. The push-wire 124 may be abrasive blast (e.g., entire outer length).

FIG. 3E illustrates a clip 126 of the plunger structure 122 interfacing with the body 110. A friction interface between the clips 126 of the plunger surface 122 and the body 110 may prevent the plunger structure 122 from deploying without being physically actuated (e.g., 0.2-0.5 deflection on both clips 126 create friction).

In some embodiments, the intracanalicular injectable applicator device 100 has a deployment mechanism (e.g., thumb deployment mechanism) disposed on the side of the intracanalicular injectable applicator device 100 (e.g., on the side of the body 110). For example, the intracanalicular injectable applicator device 100 may have one or more of roller (e.g., a side-rolling knob), a flex press actuator, slider, living hinge, and/or the like. A living hinge may be a thin flexible hinge (e.g., flexure bearing) made from the same material as two rigid pieces that the living hinge connects (e.g., plastic that is injection molded in the same orientation to be squeezed to mechanically move the intracanalicular injectable).

Figure 3F:
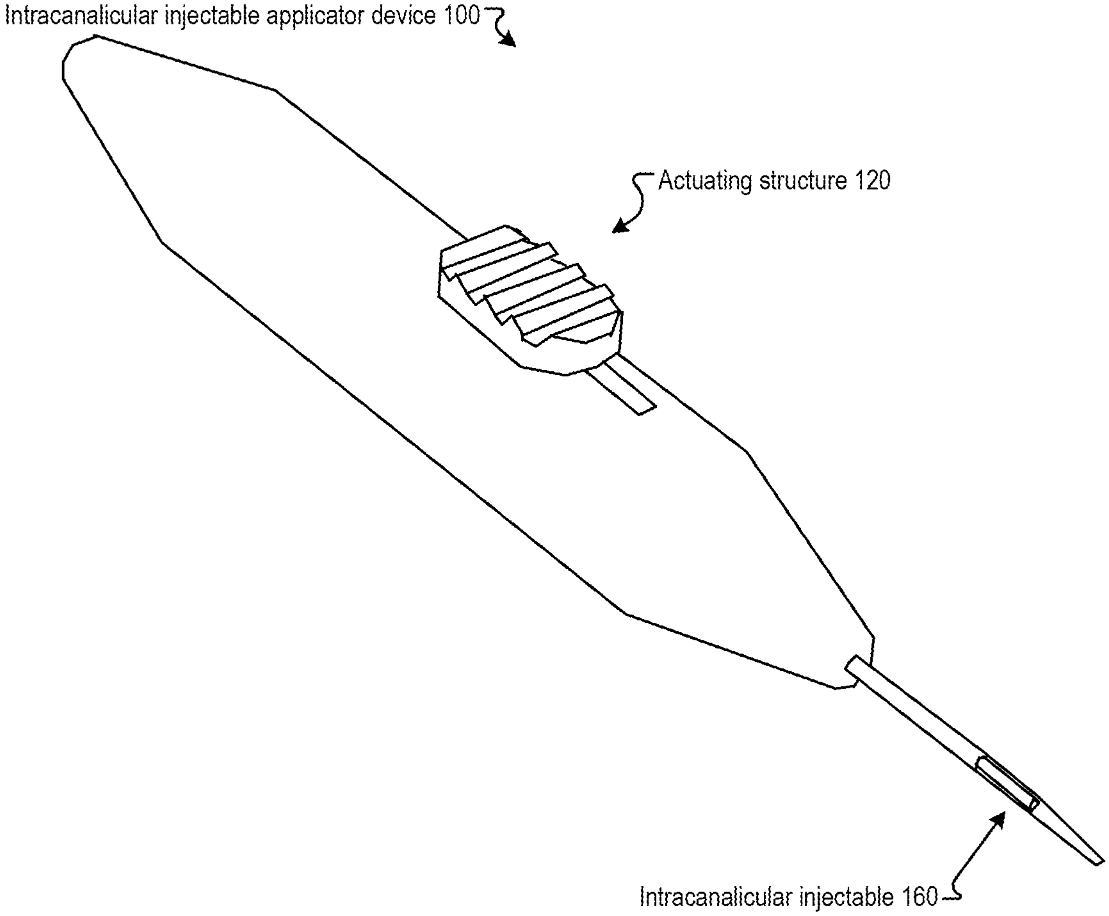
Figure 3G:
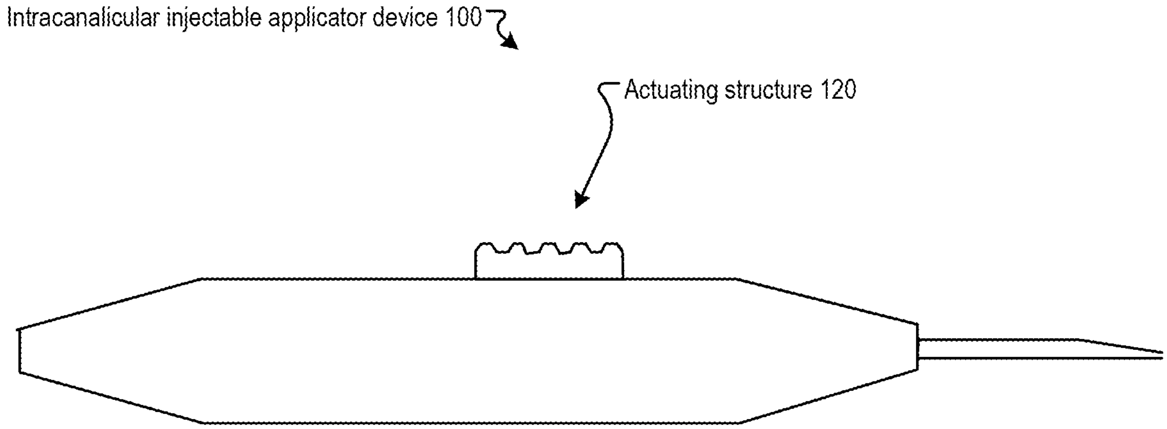

FIGS. 3F-G illustrate an intracanalicular injectable applicator device 100 that has an actuating structure 120 that has a slider feature. A user grips the body of the intracanalicular injectable applicator device 100 with a thumb and a middle finger and actuates the slider feature with an index finger. The slider feature may be part of an actuating structure 120 that has a push-wire 124.

Figure 4B:
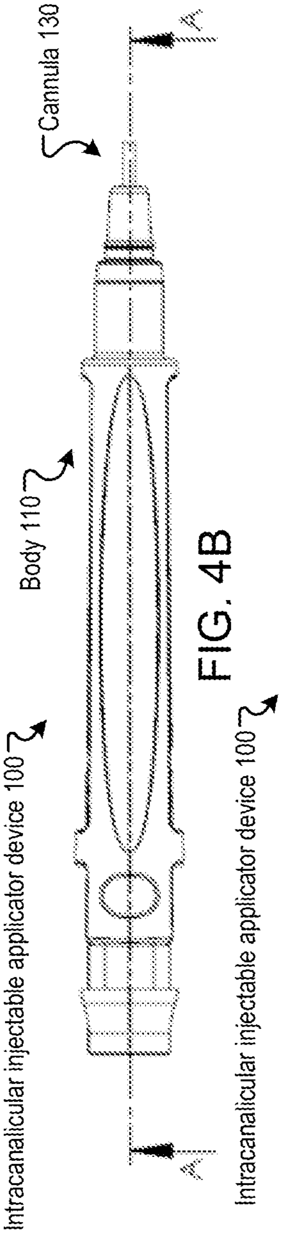
FIGS. 4A-I illustrate cannulas of intracanalicular injectable applicator devices, according to certain embodiments.
Figure 4C:
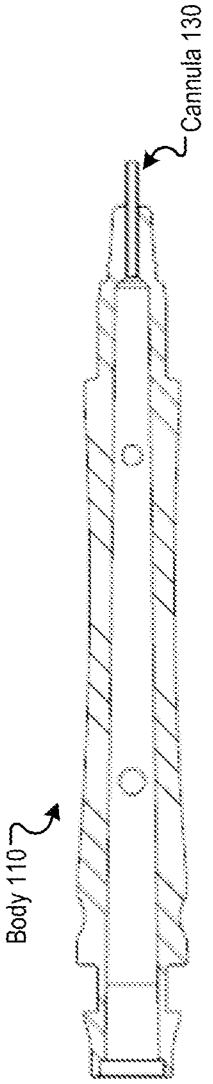
Figure 4A:
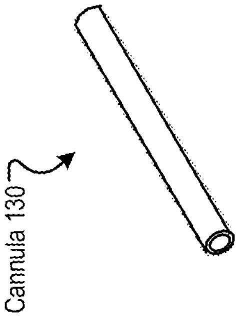

FIGS. 4A-I illustrate cannulas 130 of intracanalicular injectable applicator devices 100, according to certain embodiments. FIG. 4A illustrates a perspective view of a cannula 130. FIG. 4B illustrates a side view of cannula 130 coupled (e.g., insert welded, injection molded, adhered, glued, insert molded) to a body 110. FIG. 4C illustrates a cross-sectional view of cannula 130 coupled (e.g., insert welded, injection molded, adhered, glued, insert molded) to a body 110. The cannula 130 may be flush with a chamfer of the body 110.

In some embodiments, the cannula 130 is a 20 gauge thin wall cannula 130. Both distal ends of the cannula 10 may be cut and deburred (e.g., inside and outside diameter). The cannula 130 may be abrasive blast (e.g., entire outer length). The cannula 130 may undergo a passivation operation. In some embodiments, the cannula 130 is plastic. In some embodiments, the cannula 130 is metal.

Figure 4D:
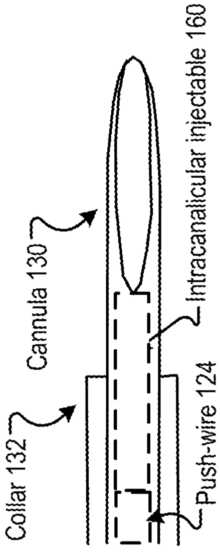
Figure 4E:
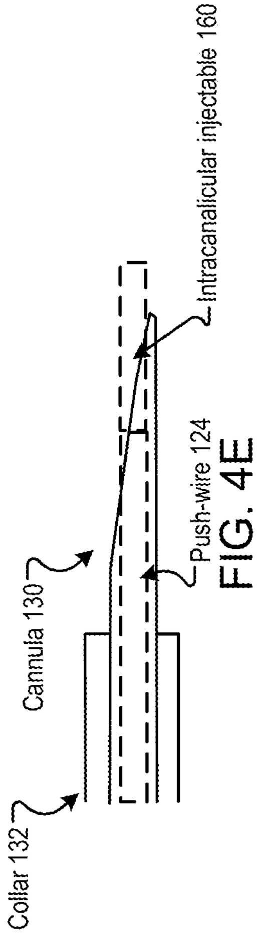
Figure 4F:
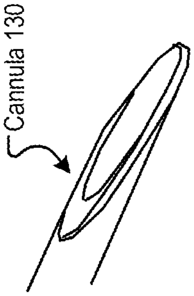
Figure 4G:
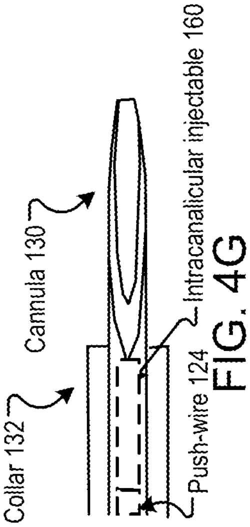
Figure 4H:
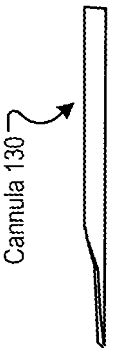
Figure 4I:
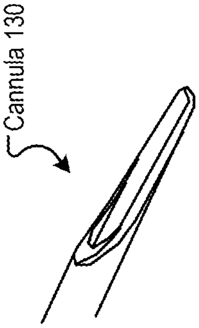

FIGS. 4D-I illustrate cannulas 130 that have a bevel. FIGS. 4D-F illustrate a cannula 130 that has a round bevel (e.g., round beveled cannula). FIGS. 4G-I illustrate a cannula 130 that has a flat bevel (e.g., flat beveled cannula). In some embodiments (e.g., instead of or in addition to having a tip structure 140), the intracanalicular injectable applicator device 100 has a collar 132 to prevent the cannula 130 from over-inserting in the punctum.

Figure 5A:
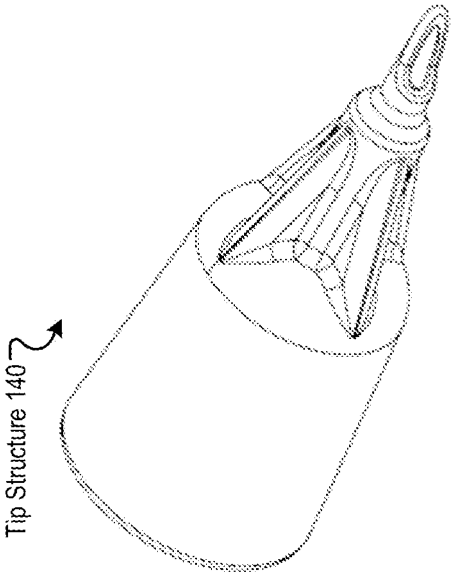
FIGS. 5A-I illustrate tip structures of intracanalicular injectable applicator devices, according to certain embodiments.
Figure 5C:
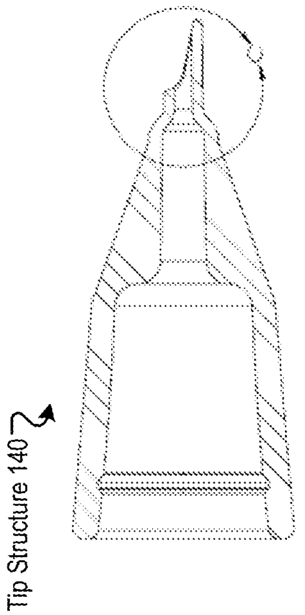
Figure 5B:
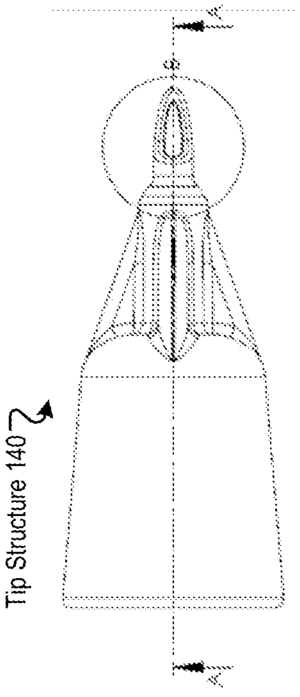
Figure 5D:
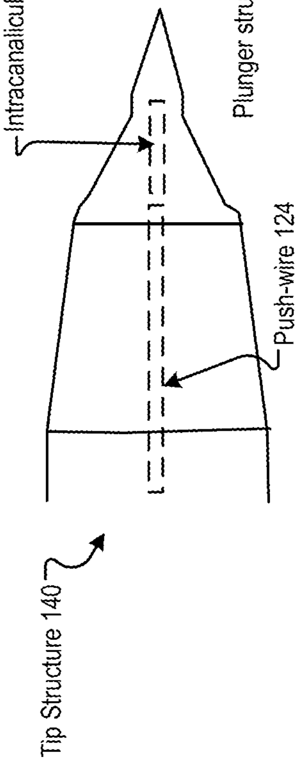
Figure 5E:
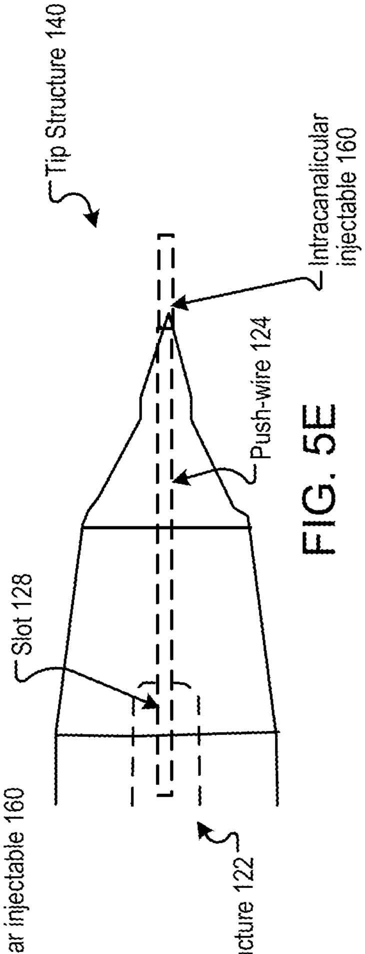
Figure 5F:
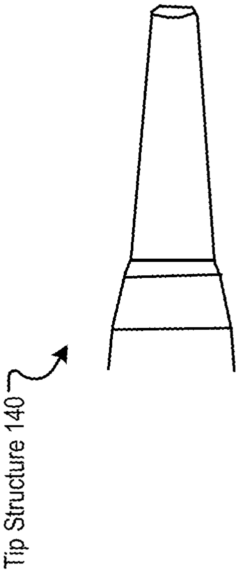
Figure 5G:
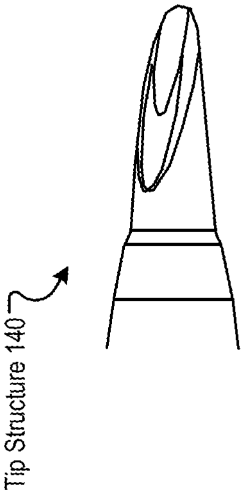
Figure 5H:
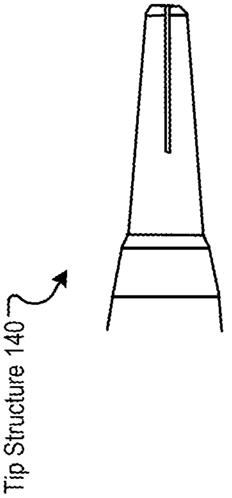
Figure 5I:
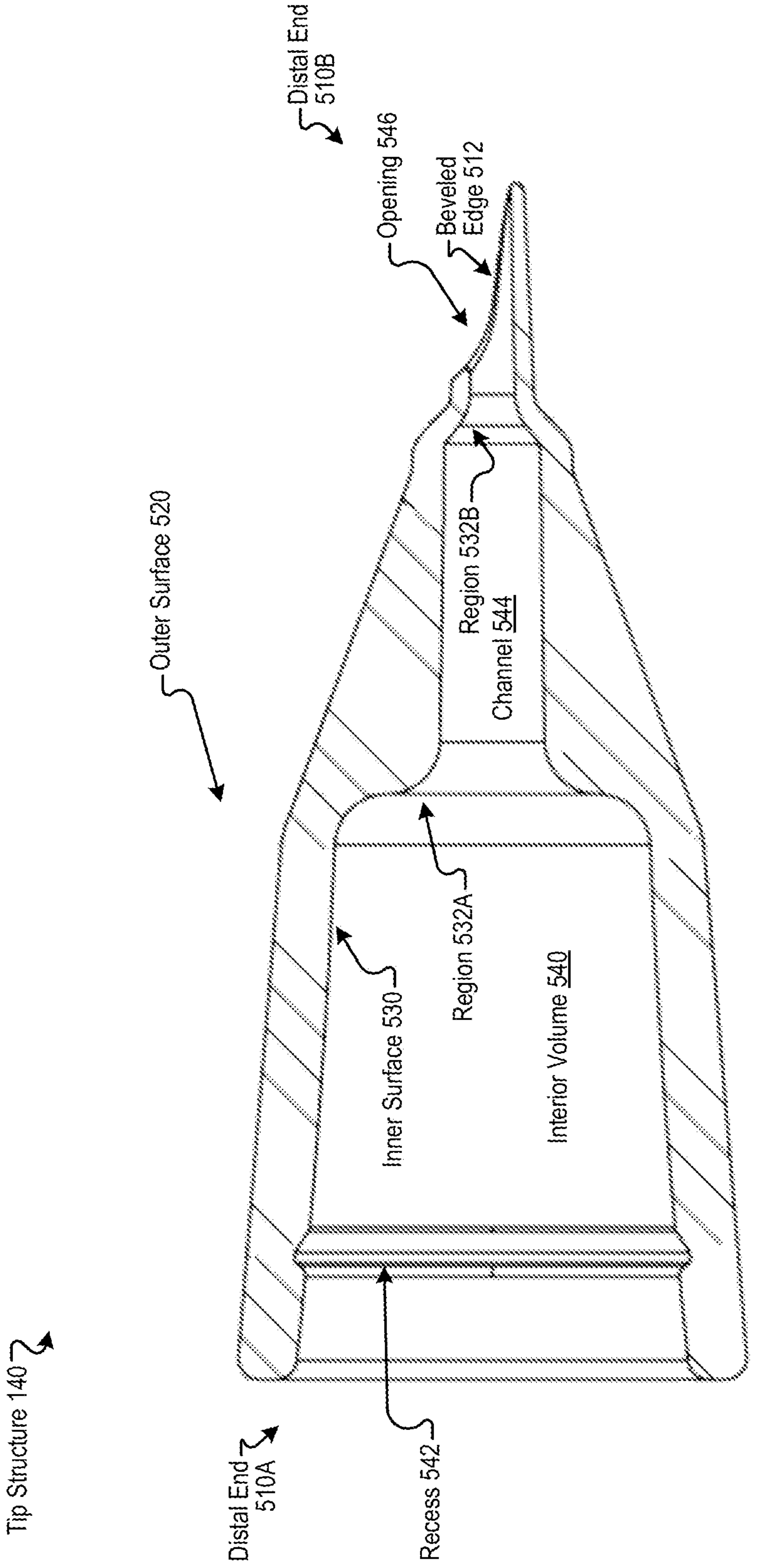

FIGS. 5A-I illustrate tip structures 140 (e.g., dilating tip, flexible tip, polymeric tip, etc.) of intracanalicular injectable applicator devices 100, according to certain embodiments. FIG. 5A is a perspective view of a tip structure 140. FIG. 5B is a side view of a tip structure 140. FIG. 5C is a cross-sectional view of a tip structure 140. FIG. 5D is a side review of a tip structure 140 prior to deploying the intracanalicular injectable 160. FIG. 5E is a side view of the tip structure with the intracanalicular injectable 160 deployed. FIGS. 5F-H illustrate distal ends (e.g., tips) of tip structure 140. FIG. 5I is a cross-sectional view of a tip structure 140.

The tip structure 140 is configured to dilate the lacrimal punctum and to deploy an intracanalicular injectable after dilating the lacrimal punctum (e.g., dilating and deploying is performed without removing the tip structure 140 from the lacrimal punctum). In some embodiments, the tip structure 140 has a flexible beveled tip that is configured to dilate the lacrimal punctum and deploy the intracanalicular injectable to a position (e.g., a repeatable location) in the canaliculus.

In some embodiments, the lacrimal punctum is 0.2 to 0.5 mm in diameter (e.g., which may be smaller than the intracanalicular injectable). The length of the vertical section of the canaliculus may be about 1.7 to 2 mm. The intracanalicular injectable may be about 2 mm in length (e.g., may be longer than the vertical section of the canaliculus). The intracanalicular injectable may hydrate and swell over time to retract and move into the vertical segment where the intracanalicular injectable may remain while being used. In some embodiments, the diameter of the distal end (e.g., tip) of the tip structure 140 (e.g., the distal end of the beveled end) may be about 0.1 to 0.4 mm. In some embodiments, the diameter of the distal end (e.g., tip) of the tip structure 140 (e.g., the distal end of the beveled end) may be about 0.2 to 0.3 mm.

The material of the tip structure 140 may be strong (e.g., stiff) enough to dilate the lacrimal punctum and flexible (e.g., mechanically soft) enough to allow an intracanalicular injectable to go through an opening in the distal end of the tip structure 140 (e.g., to enter the canaliculus via the lacrimal punctum). In some embodiments, the distal end (e.g., tip) of the tip structure 140 has a radial flexibility (e.g., flex outward, expand tip).

In some embodiments, the distal end (e.g., tip) of the tip structure 140 has a beveled end (e.g., diagonal cut, cut slant, etc.). In some embodiments, the channel through the distal end of the tip structure 140 is circular and the opening at the beveled end is an oval shape. The beveled end may allow the intracanalicular injectable to deploy into the canaliculus sooner than and not as deep as a flat end. The beveled end may come to a smaller point than a flat end and the smaller point may allow focusing the force onto the lacrimal punctum to dilate the lacrimal punctum.

The tip structure 140 may be made with one or more of a medical grade silicone rubber, class VI material, thermoplastic elastomer (TPE), fluorinated ethylene propylene (FEP), block copolymers, silicone, etc. In some embodiments, the tip structure 140 has a Shore A durometer of about 50 to about 120. In some embodiments, the tip structure 140 has a Shore A durometer of about 50 to about 110. In some embodiments, the tip structure 140 has a Shore A durometer of about 50 to about 70. In some embodiments, the tip structure 140 has a Shore A durometer of about 85 to about 110. In some embodiments, the tip structure 140 has a Shore A durometer of about 90 to about 95. In some embodiments, the tip structure 140 has a Shore A durometer of about 95. The distal end of the tip structure 140 may facilitate delivery of an intracanalicular injectable (e.g., cylindrical ophthalmic insert of about 0.45 to 0.54 mm diameter and/or about 2.92 to 3.08 mm length) into the inferior canaliculus (e.g., tear duct) or the superior canaliculus (e.g., tear duct). The tear duct may have an average diameter of 0.4 mm and may expand to 0.7 to 0.9 mm once the distal end of the tip structure 140 is fully inserted. The distal end of the tip structure 140 may be stiff enough to find and dilate the opening of the tear duct by being inserted. The distal end of the tip structure 140 may remain in the tear duct as the intracanalicular injectable is deployed through the mouth (e.g., opening) of the distal end of the tip structure 140. The distal end of the tip structure 140 may be flexible to allow the intracanalicular injectable of a first threshold diameter (e.g., 0.54 mm) to push through and also small enough to retain an intracanalicular injectable of a second threshold diameter (e.g., 0.45 mm) from falling out. The intracanalicular injectable may be positioned 0.2 to 0.8 mm below the opening of the tear duct after deployment.

In some embodiments, the tip structure 140 has a silicone tip. After the entire tip is seated in the canaliculus, the intracanalicular injectable is pushed through the elastic silicone opening. The intracanalicular injectable dilates the canaliculus is the intracanalicular injectable approaches the final position of the intracanalicular injectable. The diameter at the distal end of the tip structure 140 may be about 0.3-0.5 mm. The maximum diameter of the tip of the tip structure 140 may be about 0.7-0.9 mm. The maximum placement depth may be about 1-5 mm. The durometer of the tip structure 140 may be firm for finding punctum and anchoring the tip of the tip structure. The durometer of the tip structure 140 may be flexible for deploying the intracanalicular injectable. In some embodiments, the distal end (e.g., tip) of the tip structure 140 has a flat tip (see FIG. 5F), a beveled tip (see FIG. 5G), and/or a slit tip (see FIG. 5H).

In some embodiments, the intracanalicular injectable applicator device 100 has a cannula 130 that is beveled. The cannula 130 may be rounded to be used to find a punctum and dilate the punctum to receive the cannula 130. The intracanalicular injectable may be deployed once the bevel of the cannula 130 is no longer exposed. A metal collar may prevent over-insertion of the intracanalicular injectable applicator device 100 into the punctum. In some embodiments, the width of the cannula 130 at the tip is about 0.1 to 0.15 mm. In some embodiments, the outs-die diameter of the cannula is about 0.5 to 1.5 mm. In some embodiments, the maximum insertion depth is about 5 to 6 mm. In some embodiments, the flat tip of the cannula 130 creates a blunt surface to reduce potential tissue damage. In some embodiments, the cannula 130 has a two angle bevel design that allows the intracanalicular injectable to be deposited closer to the punctum opening (e.g., 0.5 to 0.75 mm deep).

Referring to FIG. 5I, the tip structure 140 may include distal ends 510A and 510B, outer surface 520, and inner surface 530. The outer surface 520 may be sloped (e.g., curved, tapered, etc.) from distal end 510A to distal end 510B (e.g., which allows a user to view the lacrimal punctum during use). The inner surface 530 may form an inner volume 540, recess 542, and a channel 544. The inner surface 530 may include regions 532A-B that are one or more of sloped, curved, tapered, funnel-shaped, etc. to go from a larger diameter closer to distal end 510A to a smaller diameter closer to distal end 510B.

In some embodiments, a first distal end of a cannula 130 is coupled to body 110 and a second distal end of cannula 130 is configured to be secured by the inner surface 530 in channel 544 of the tip structure 140. In some embodiments, the region 532A guides the second distal end of cannula 130 into the channel 544. In some embodiments, the second distal end of cannula 130 abuts a portion of region 532B. The region 532B may guide the intracanalicular injectable from the cannula 130 to the opening 546 (e.g., oval opening) in the beveled edge 512. A portion of the inner surface 5530 is disposed over a portion of the body 110 (e.g., is secured to the body 110 via a friction fit). In some embodiments, the recess 542 of the tip structure 140 interfaces with (e.g., snaps on) a protrusion (e.g., an annular ring) of the body 110.

In some embodiments, the tip structure 140 includes a distal end 510A configured to attach to a body 110 of the intracanalicular injectable applicator device 100. The tip structure 140 may include an inner surface 530 forming a recess (e.g., channel 544) configured to receive a distal end of a cannula 130 (e.g., the other distal end of the cannula 130 is coupled to the body 110). The inner surface 530 of the tip structure 140 and the cannula 130 may mate with each other (e.g., friction fit) to prevent the cannula 130 from moving. The tip structure 140 may include a distal end 510B that includes a beveled edge 512 (e.g., beveled tip) configured to be inserted in a lacrimal punctum to dilate the lacrimal punctum and to deploy an intracanalicular injectable from the cannula 130 into the canaliculus via the lacrimal punctum.

Figure 6A:
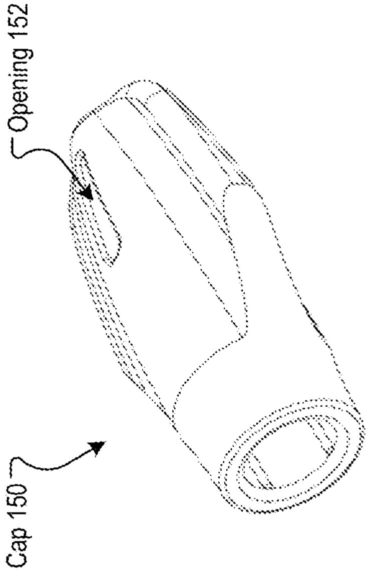
FIGS. 6A-F illustrate caps of intracanalicular injectable applicator devices, according to certain embodiments.

FIGS. 6A-F illustrate a cap 150 of an intracanalicular injectable applicator device 100, according to certain embodiments. FIG. 6A is a perspective view of a cap 150.

Figure 6B:
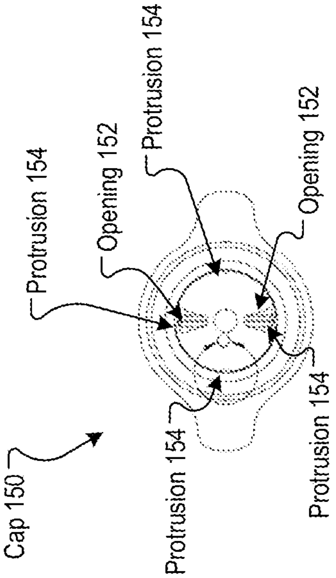
Figure 6C:
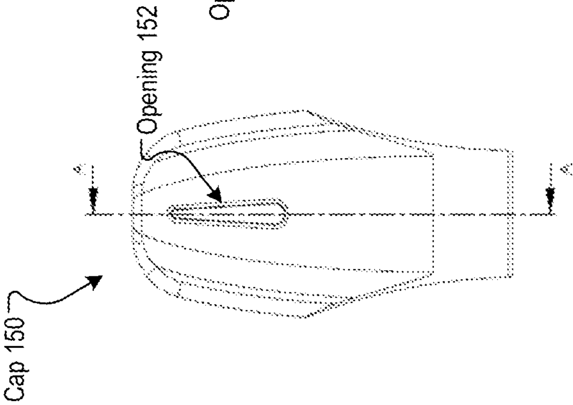
Figure 6D:
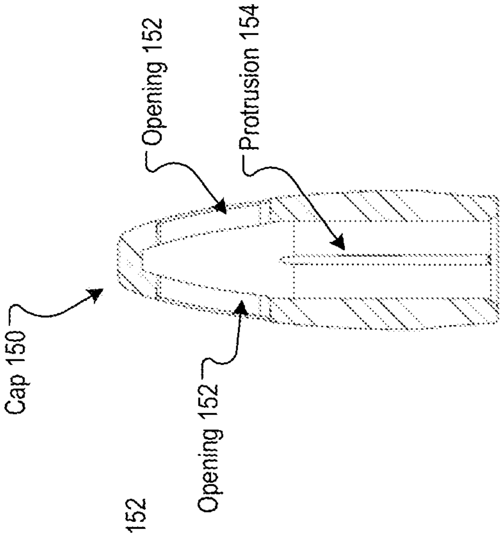
Figure 6E:
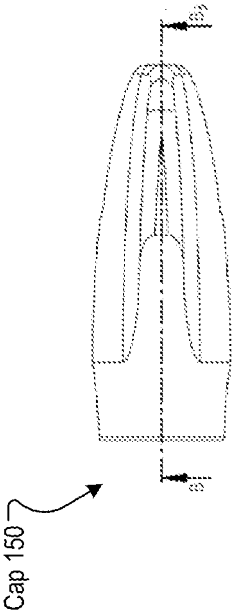
Figure 6F:
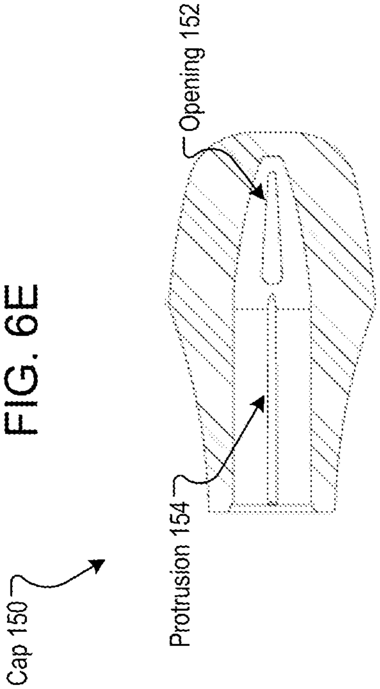

FIG. 6B is a bottom view of a cap 150. FIG. 6C is a first side view of a cap 150. FIG. 6D is a first cross-sectional view of a cap 150. 6E is a second side view of a cap 150 (e.g., rotated 90 degrees compared to FIG. 6C). FIG. 6F is a second cross-sectional view of a cap 150 (e.g., rotated 90 degrees compared to FIG. 6D).

The cap 150 may include one or more (e.g., two) openings 152 (e.g., vents).

The cap 150 may lightly press fit onto the body 110. The cap 150 may not have a grease or mold release. The cap 150 may have one or more protrusions 154 from an inside surface (e.g., see FIGS. 6B, 6D, and 6F) that provide the press fit with the body 110. In some embodiments, the cap 150 includes four protrusions 154 that are each 90 degrees apart in the inside surface that provide the press fit with the body.

Figure 7:
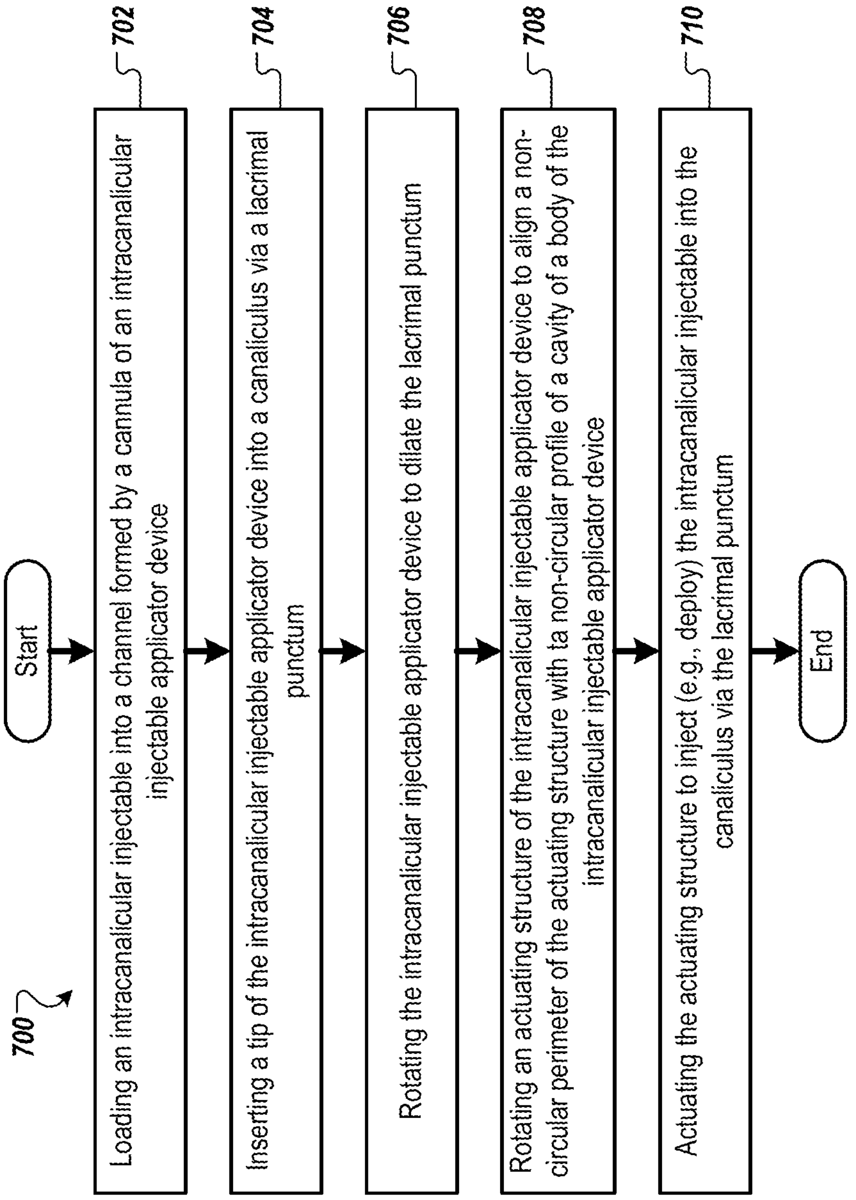
FIG. 7 illustrates a method of treatment of administering an intracanalicular injectable using an intracanalicular injectable applicator device, according to certain embodiments.

FIG. 7 illustrates a method 700 of treatment of administering an intracanalicular injectable using an intracanalicular injectable applicator device, according to certain embodiments. Although shown in a particular sequence or order, unless otherwise specified, the order of the operations can be modified. Thus, the illustrated embodiments should be understood only as examples, and the illustrated operations can be performed in a different order, and some operations can be performed in parallel. Additionally, one or more operations can be omitted in various embodiments. Thus, not all operations are required in every embodiment.

At block 702, an intracanalicular injectable is loaded into a channel (e.g., lumen) formed by a cannula of an intracanalicular injectable applicator device. The channel is aligned with a cavity formed by a body of the intracanalicular injectable applicator device. An actuating structure of the intracanalicular injectable applicator device is partially disposed in the cavity of the body and partially disposed in the channel of the cannula.

At block 704, a distal end (e.g., tip, beveled edge, etc.) of a tip structure of the intracanalicular injectable applicator device is inserted into a canaliculus via a lacrimal punctum to dilate the lacrimal punctum.

At block 706, the intracanalicular injectable applicator device is rotated to further dilate the lacrimal punctum to receive an intracanalicular injectable.

At block 708, the actuating structure is rotated to align a non-circular perimeter of the actuating structure (e.g., oval-shaped perimeter portion of the plunger structure) with a non-circular profile of the cavity of the body (e.g., oval-shaped portion of the cavity of the body).

At block 710, the actuating structure is actuated (e.g., by pressing on the distal end of the actuating structure) to inject (e.g., deploy) the intracanalicular injectable into the canaliculus via the lacrimal punctum.

In some embodiments, method 700 includes more or less operations than those shown in FIG. 7. In some examples, method 700 may include the inserting of block 704 and the actuating of block 710 (e.g., the intracanalicular injectable applicator device is pre-loaded).

FIGS. 8A-12G illustrate components of intracanalicular injectable applicator devices 100. The intracanalicular injectable applicator devices 100 of FIGS. 8A-12G may have the same or similar functionality or structure as the intracanalicular injectable applicator devices 100 described in FIGS. 1A-7. Features in the FIGS. may have the same or similar functionality as other features in other FIGS. that have a similar reference number.

Figures 8A, 8B, 8C, 8D:
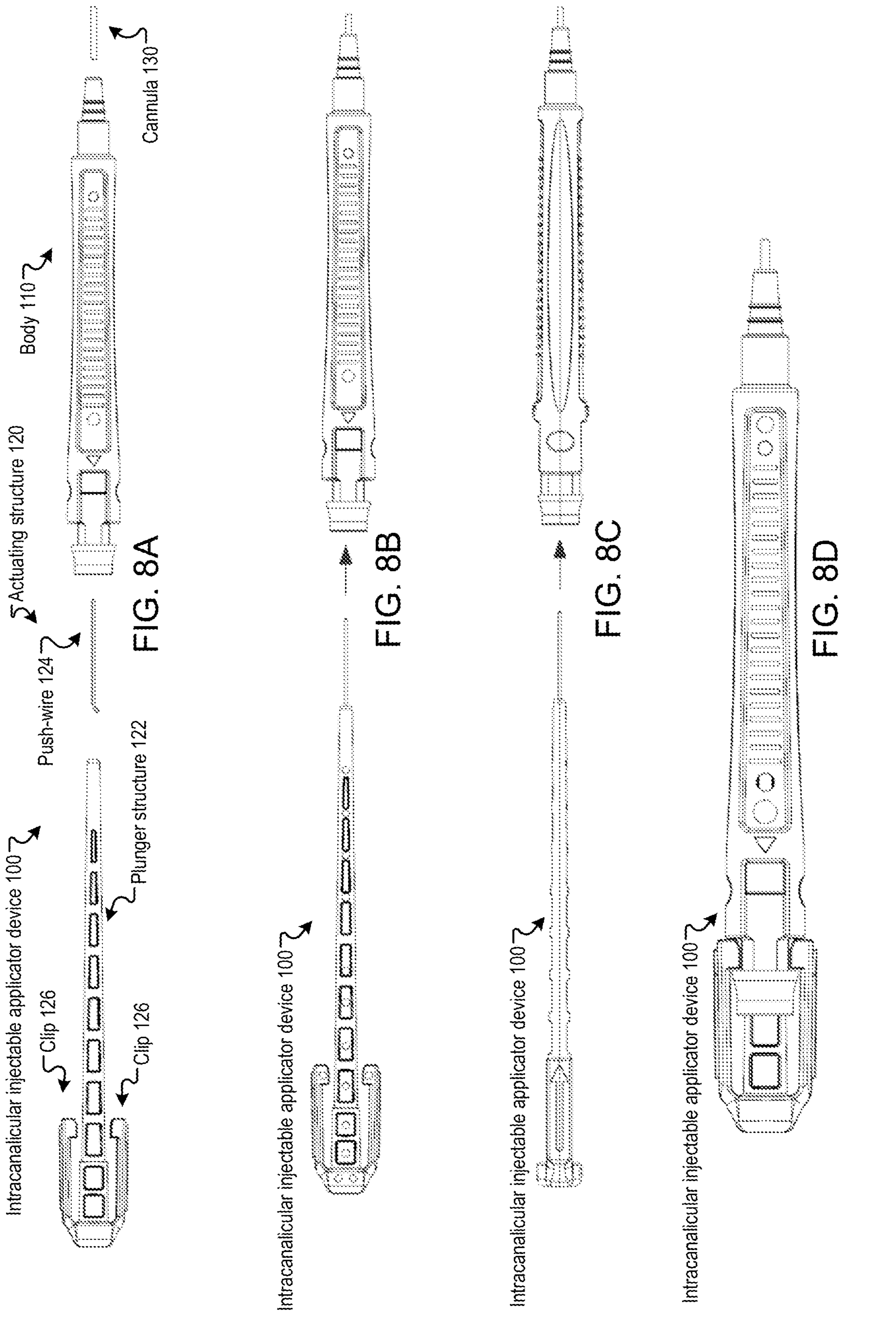
FIGS. 8A-I illustrate intracanalicular injectable applicator devices, according to certain embodiments.
Figure 8E:
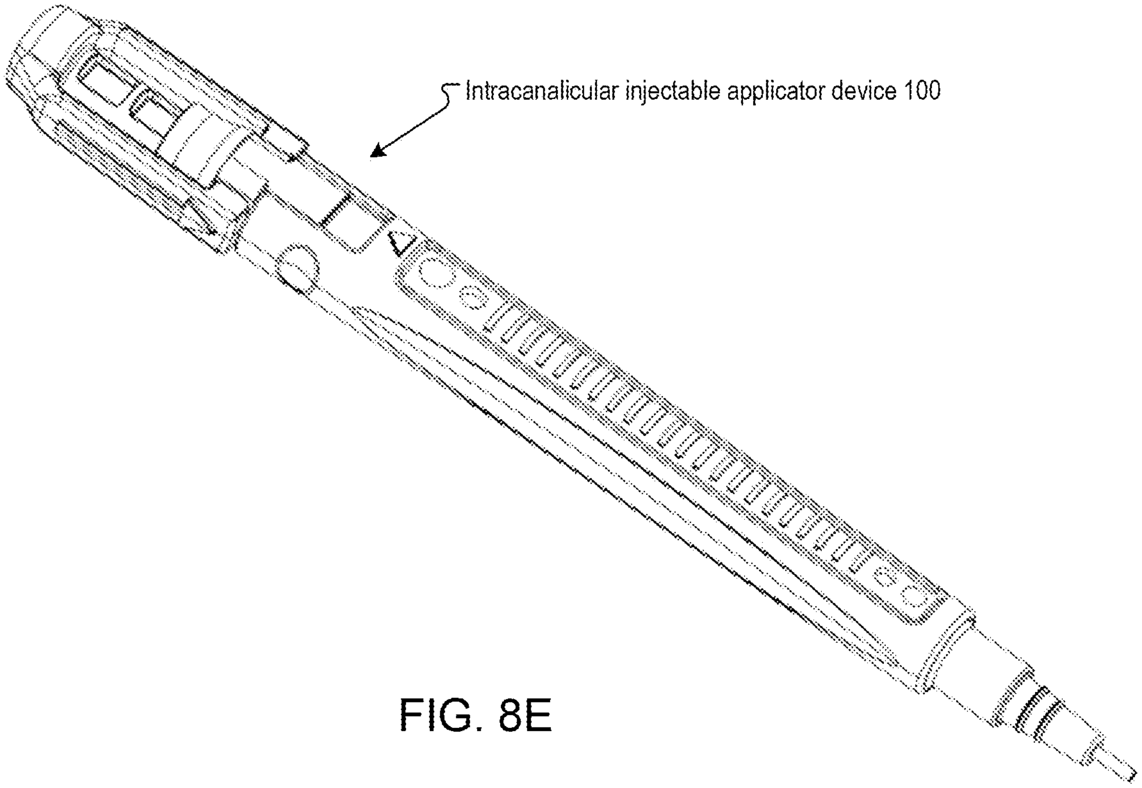
Figure 8F:
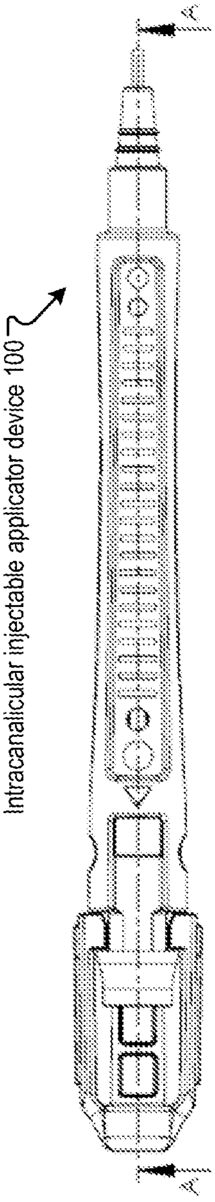
Figure 8G:
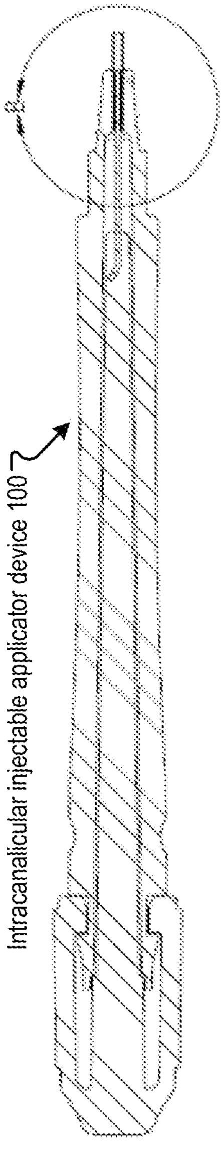
Figure 8H:
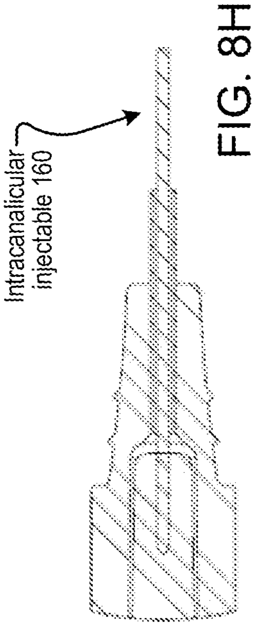
Figure 8I:
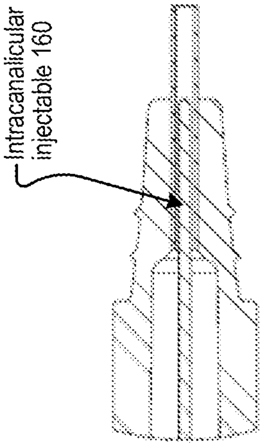

FIGS. 8A-I illustrate intracanalicular injectable applicator devices 100, according to certain embodiments. FIG. 8A illustrates an exploded view of the intracanalicular injectable applicator device 100. FIG. 8B illustrates a side view of the actuating structure 120 to be inserted into the body 110 of the intracanalicular injectable applicator device 100. FIG. 8C illustrates a top view of the actuating structure 120 to be inserted into the body 110 of the intracanalicular injectable applicator device 100. FIG. 8D illustrates a side view of an assembled intracanalicular injectable applicator device 100. FIG. 8E illustrates a perspective view of an intracanalicular injectable applicator device 100. FIG. 8F illustrates a side view of an intracanalicular injectable applicator device 100. FIG. 8G illustrates a cross-sectional view of an intracanalicular injectable applicator device 100 (e.g., of FIG. 8F). FIG. 8H illustrates a cross-sectional view of a distal end of the body 110 deploying an intracanalicular injectable 160 (e.g., detailed view of FIG. 8G). FIG. 8I illustrates a cross-sectional view of a distal end of the body 110 including an intracanalicular injectable 160 in a loaded position (e.g., detailed view of FIG. 8G).

The body 110 may have protrusions (e.g., ridges) to prevent slipping of the intracanalicular injectable applicator device 100 from the hand of the user.

Figure 9A:
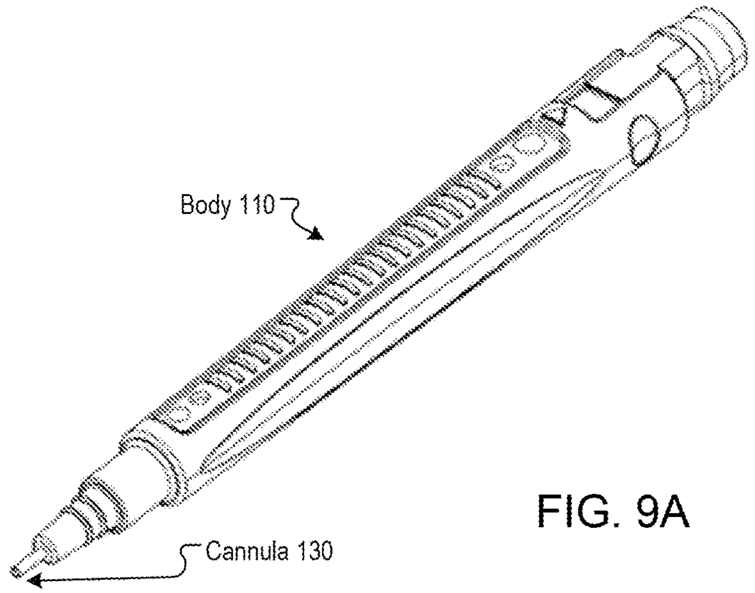
FIGS. 9A-I illustrate a body of an intracanalicular injectable applicator device, according to certain embodiments.
Figure 9B:
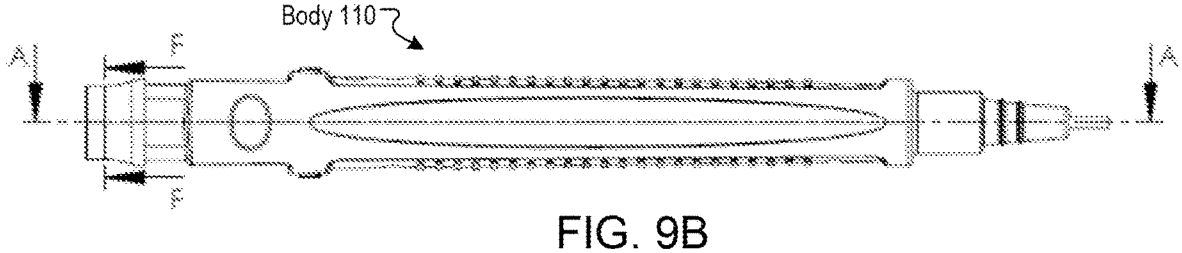
Figure 9C:
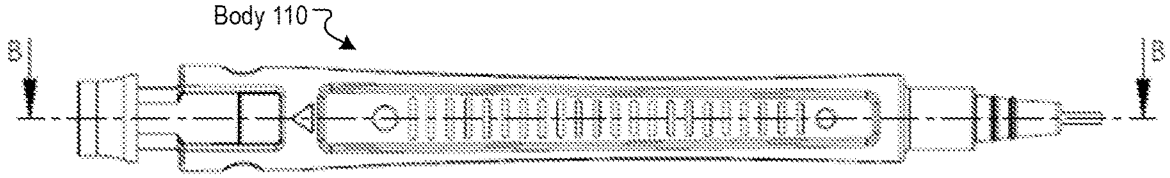
Figure 9D:
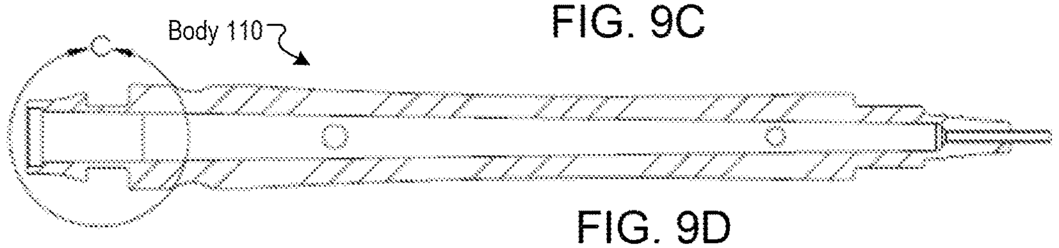
Figure 9E:
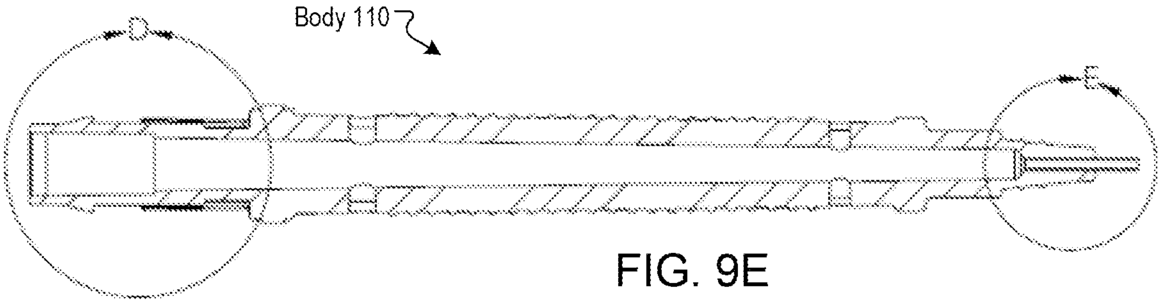
Figure 9F:
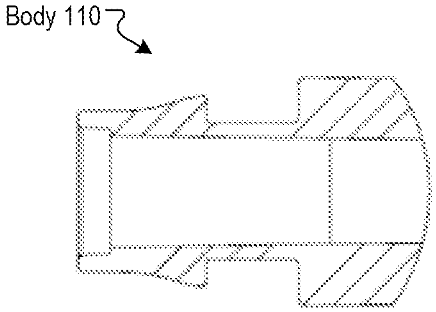
Figure 9G:
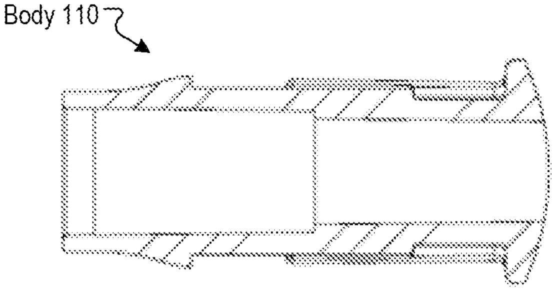
Figure 9H:
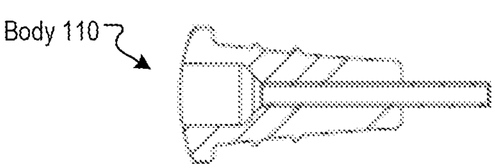
Figure 9I:
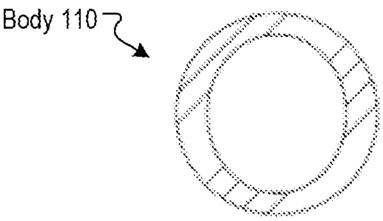

FIGS. 9A-I illustrate a body 110 of an intracanalicular injectable applicator device 100, according to certain embodiments. FIG. 9A illustrates a perspective view of a body 110 of an injectable applicator device 100 coupled to a cannula 130. FIG. 9B illustrates a side view of a body 110 of an injectable applicator device 100 coupled to a cannula 130. FIG. 9C illustrates a top view of a body 110 of an injectable applicator device 100 coupled to a cannula 130. FIG. 9D illustrates a cross-sectional view of a body 110 of an injectable applicator device 100 coupled to a cannula 130 (e.g., section A-A of FIG. 9B). FIG. 9E illustrates a cross-sectional view of a body 110 of an injectable applicator device 100 coupled to a cannula 130 (e.g., section B-B of FIG. 9C). FIG. 9F illustrates a cross-sectional view of a distal end of body 110 of an injectable applicator device 100 (e.g., detail C of FIG. 9D). FIG. 9G illustrates a cross-sectional view of a distal end of body 110 of an injectable applicator device 100 (e.g., detail D of FIG. 9E). FIG. 9H illustrates a cross-sectional view of a distal end of body 110 of an injectable applicator device 100 (e.g., detail E of FIG. 9E). FIG. 9I illustrates a cross-sectional view of body 110 of an injectable applicator device 100 (e.g., section F-F of FIG. 9B).

In some embodiments, an outer surface of the cannula 130 is roughened (e.g., via sandblasting) so that the cannula 130 and body 110 secure to each other greater than if the cannula 130 had a smoother outer surface. In some embodiments, the cannula 130 is adhered (e.g., glued), insert molded (e.g., injection molded), and/or the like to the body 110.

FIGS. 10A-G illustrate actuating structures 120 of intracanalicular injectable applicator devices 100, according to certain embodiments. FIG. 10A illustrates a perspective view of an actuating structure 120. FIG. 10B illustrates a top view of an actuating structure 120. FIG. 10C illustrates a cross-sectional view of an actuating structure 120 (e.g., section A-A of FIG. 10B). FIG. 10D illustrates a side view of an actuating structure 120. FIG. 10E illustrates a push wire 124 of the actuating structure 120. FIG. 10F illustrates a cross-sectional view of a distal end of an actuating structure 120 (e.g., detail B of FIG. 10C). FIG. 10G illustrates a cross-sectional view of a distal end of an actuating structure 120 (e.g., section E-E of FIG. 10D).

In some embodiments, a length of the push-wire 124 is substantially straight (e.g., disposed about a longitudinal axis) a distal end of push-wire 124 is bent (e.g., not disposed along the longitudinal axis). The bent distal end of the push-wire 124 may be insert molded (e.g., injection molded) to the plunger structure 122 (e.g., to secure to each other greater than if the distal end of the push-wire 124 were not bent). In some embodiments, the push-wire 124 is roughened (e.g., sandblasted) so that the push-wire 124 and the plunger structure 122 secure to each other greater than if the push-wire 124 had a smooth outer surface.

Figure 11A:
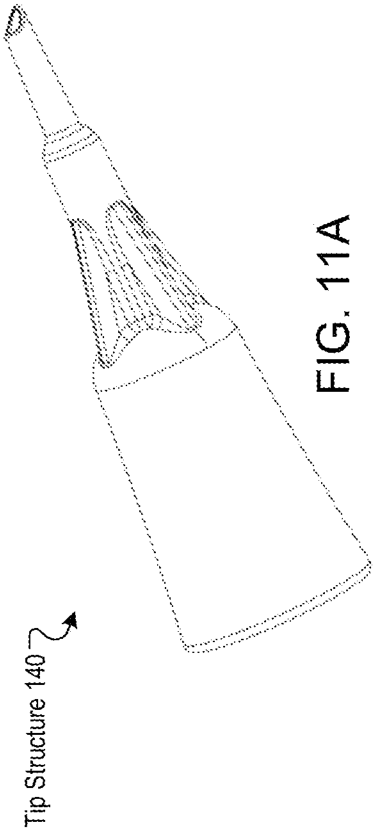
FIGS. 11A-E illustrate tip structures of intracanalicular injectable applicator devices, according to certain embodiments.
Figure 11B:
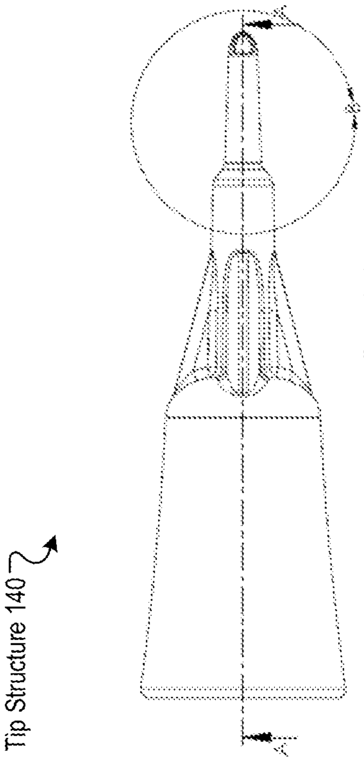
Figure 11C:
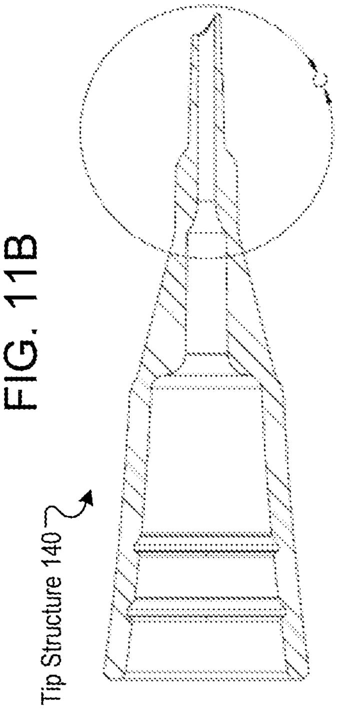
Figure 11D:
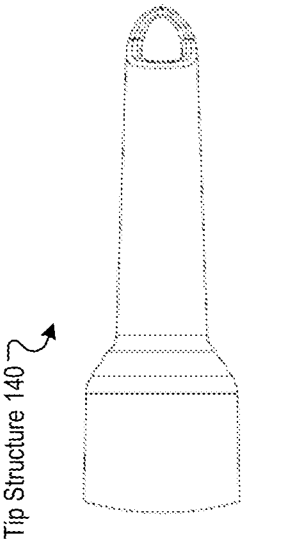
Figure 11E:
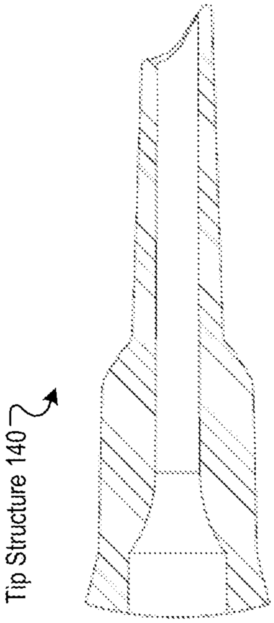

FIG. 11A-E illustrate tip structures 140 of intracanalicular injectable applicator devices 100, according to certain embodiments. FIG. 11A is a perspective view of a tip structure 140. FIG. 11B is a top view of a tip structure 140. FIG. 11C is a cross-sectional view of a tip structure 140 (e.g., section A-A of FIG. 11B). FIG. 11D is a top view of a distal end of a tip structure 140 (e.g., detail B of FIG. 11B). FIG. 11E is a cross-sectional view of a distal end of a tip structure 140 (e.g., detail C of FIG. 11C).

In some embodiments, the tip structure 140 is made of a translucent (e.g., transparent, clear) material to allow the user to visualize the intracanalicular injectable 160 as the intracanalicular injectable 160 is passing from the tip structure 140 into the canaliculus (e.g., to provide more user feedback and control).

Figure 12A:
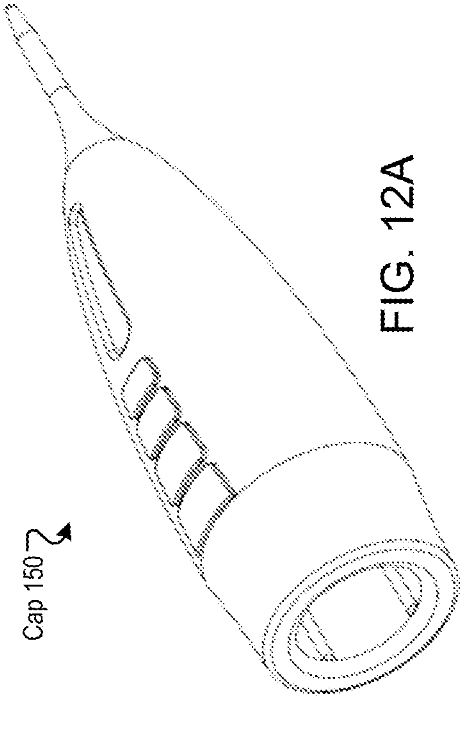
FIGS. 12A-G illustrate caps of intracanalicular injectable applicator devices, according to certain embodiments.
Figure 12B:
Figure 12C:
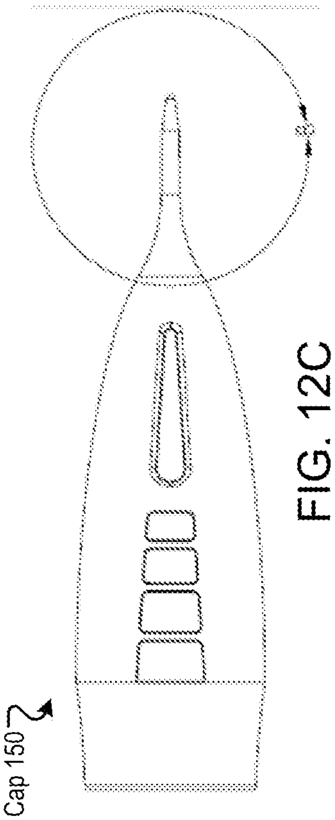
Figure 12D:
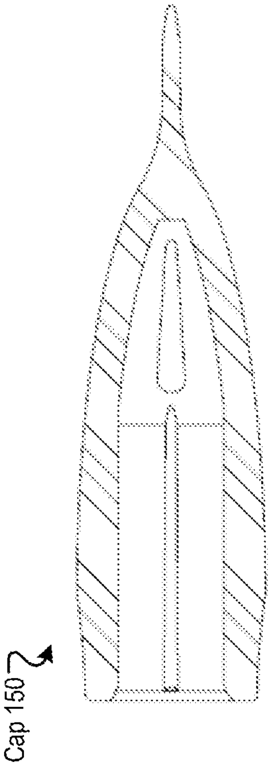
Figure 12E:
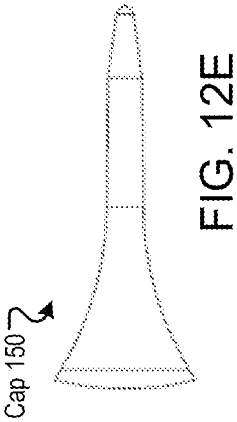
Figure 12F:
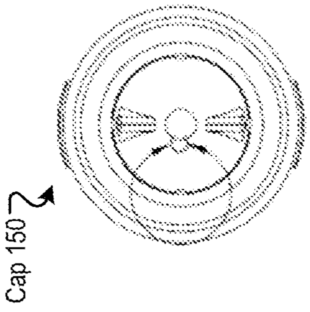
Figure 12G:
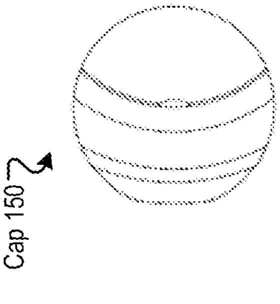

FIGS. 12A-G illustrate caps 150 of intracanalicular injectable applicator devices 100, according to certain embodiments. FIG. 12A is a perspective view of a cap 150. FIG. 12B is a side view of a cap 150. FIG. 12C is a top view of a cap 150. FIG. 12D is a cross-sectional view of a cap 150 (e.g., section A-A of FIG. 12B). FIG. 12E is a top view of a cap 150 (e.g., detail B of FIG. 12C). FIG. 12F is a rear view of a cap 150. FIG. 12G is a rear view of a cap 150 (e.g., detail C of FIG. 12F).

In some embodiments, the outer surface of the cap 150 has protrusions (e.g., a series of small rectangular-shaped extrusions along the face of the cap 150). The protrusions provide additional grip to the user when removing the cap 150 from the body 110. In some embodiments, the body 110 has protrusions (e.g., a series of small rectangular shaped extrusions along the length of the body 110) that provide additional grip to prevent finger slippage when performing dilation and injection (e.g., insertion).

In some embodiments, the cap 150 (e.g., cap dilator, protective cap) has a tapered dilator that can be used to dilate the punctal opening facing in the distal direction. The cap 150 can be used by the physician before the injection (e.g., insertion) procedure to widen the punctal opening and canaliculi prior to the injection procedure (e.g., insertion procedure). Since the cap 150 is attached (e.g., removably coupled, removably attached) to the body 110, the user can utilize the ergonomic body 110 to manipulate the dilator to achieve dilation.

A small segment (e.g., of the distal end) of the dilator tip of the cap 150 is tapered so that the distal end of the tip can be small enough (e.g., form a point small enough) to find and initially enter the punctum. Behind the tapered segment is a straight segment of uniform diameter (e.g., the diameter remains constant for a section before continuing to taper to a larger diameter) which allows the dilator of the cap 150 to progress deeper and dilate the full length of the canaliculus (e.g., dilate the entire length of the canaliculus equal to the length of the intracanalicular injectable 160) where the intracanalicular injectable 160 is to reside. The tip of the cap 150 may be referred to as a second tip structure and the straight segment of the cap 150 may be referred to as a substantially constant diameter segment that is adjacent to the second tip structure of the cap 150. Conventional dilators have a single taper and dilate only the punctum. The cap 150 dilates both the punctum and the canaliculus. Dilating a longer segment of the vertical canaliculus makes it easier for the user to progress the intracanalicular injectable 160 through the canaliculus.

In some embodiments, for a lacrimal punctum that has a width that is less than a threshold width, the tip of the cap 150 is used for a first dilation procedure to partially dilate the lacrimal punctum and canaliculus and then the tip structure 140 is used for a second dilation procedure to finish dilating the lacrimal punctum and/or canaliculus to inject (e.g., deploy, insert) the intracanalicular injectable 160 into the canaliculus. In some embodiments, for a lacrimal punctum that has a width that is greater than a threshold width, the tip structure 140 is used for a dilation procedure to dilate the lacrimal punctum and/or canaliculus to inject (e.g., deploy, insert) the intracanalicular injectable 160 into the canaliculus (e.g., without use of the cap 150 to dilate the lacrimal punctum and/or canaliculus).

Figure 12H:
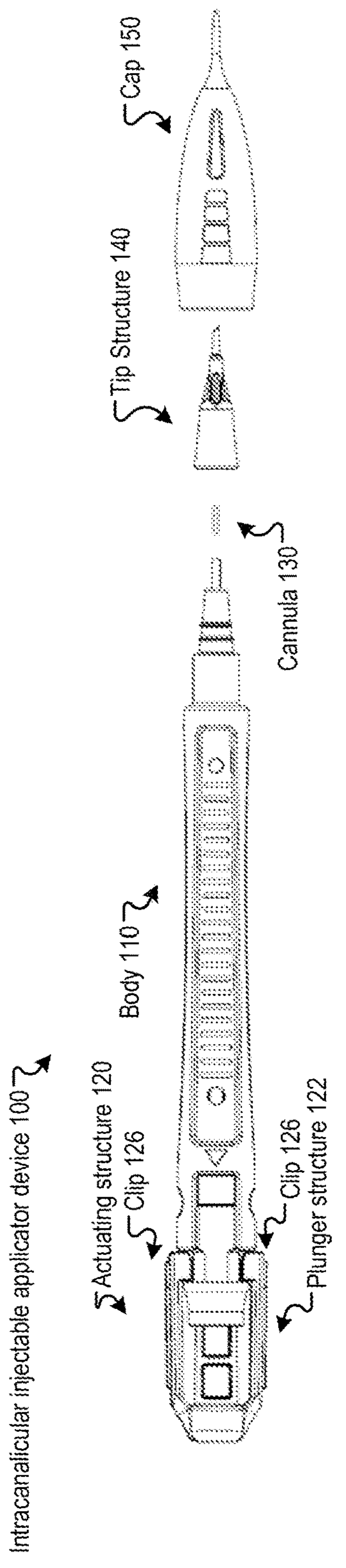
FIGS. 12H-I illustrate intracanalicular injectable applicator devices, according to certain embodiments.
Figure 12I:
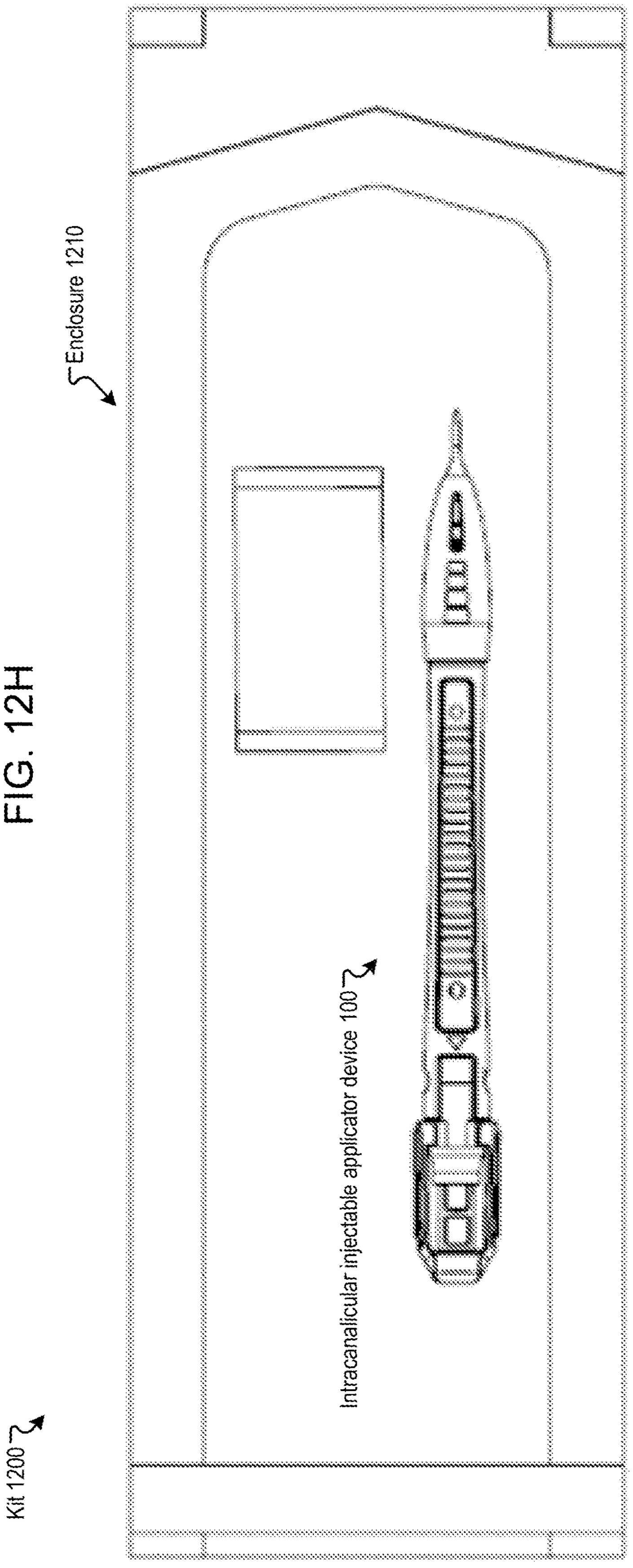

FIG. 12H-I illustrate intracanalicular injectable applicator devices 100, according to certain embodiments. FIG. 12H illustrates an exploded view of an intracanalicular injectable applicator devices 100. FIG. 12I illustrates a kit 1200 that includes an intracanalicular injectable applicator devices 100 disposed in an enclosure 1210. In some embodiments, the kit 1200 includes an enclosure 1210 to house components. The components may include an intracanalicular injectable applicator device 100 and an intracanalicular injectable (e.g., intracanalicular injectable loaded into the intracanalicular injectable applicator device 100 in the locked position and with a cap 150 placed on the body 110 in the kit 1200, intracanalicular injectable separate from the intracanalicular injectable applicator device 100 in the kit 1200). The enclosure 1210 may be a foil pouch. The components in the kit 1200 may include a desiccant.

In certain embodiments, the injectable (e.g., intracanalicular injectable 160, insert, depot, etc.) comprises a therapeutic agent. In some embodiments, the injectable (e.g., intracanalicular injectable 160, insert, etc.) is an injectable medication or injectable biologic to be administered by a physician for prevention, treatment, or cure of a disease or condition of a patient. The therapeutic agent can be a prostaglandin antagonist, such as travoprost, bimatoprost or latanoprost; a glucocorticoid such as dexamethasone or a pharmaceutically acceptable salt thereof; a cyclosporine or cyclosporin derivative or an adenine mimetic such as trabodenoson.

Therapeutic agents also include, for example, agents for treating conditions that may result from inflammatory or abnormal vascular conditions, retinal vein occlusion, geographic atrophy, retinitis pigmentosa, retinoblastoma, etc. For cancer, agents may be, e.g., anti-cancer drugs, anti-VEGFs, or drugs known for use in cancer treatment.

Therapeutic agents may be those that are, e.g., anti-VEGF, blocks VEGFR1, blocks VEGFR2, blocks VEGFR3, anti-PDGF, anti-angiogenesis, sunitinib, E7080, Takeda-6d, tivozanib, regorafenib, sorafenib, pazopanib, axitinib, nintedanib, cediranib, vatalanib, motesanib, macrolides, sirolimus, everolimus, tyrosine kinase inhibitors (TKIs), imatinib, gefinitib (IRESSA), toceranib (PALLADIA), erlotinib (TARCEVA), lapatinib (TYKERB) nilotinib, bosutinib neratinib, lapatinib, vatalanib, dasatinib, erlotinib, gefitinib, imatinib, lapatinib, lestaurtinib, nilotinib, semaxanib, toceranib, or vandetanib.

The therapeutic agent may comprise a macromolecule, for example an antibody or antibody fragment. The therapeutic macromolecule may comprise a VEGF inhibitor, for example ranibizumab, the active ingredient in the commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ (ranibizumab), Eylea™ (VEGF Trap), Avastin™ (bevacizumab), Macugen™ (pegaptanib). Platelet derived growth factor (PDGF) inhibitors may also be delivered, e.g. Fovista™, an anti-PGDF aptamer.

The therapeutic agent may comprise small molecules such as of a steroid or corticosteroid and analogues thereof. For example, the therapeutic corticosteroid may comprise one or more of triamcinalone, triamcinalone acetonide, dexamethasone, dexamethasone acetate, fluocinolone, fluocinolone acetate, loteprednol etabonate, or analogues thereof. Alternatively or in combination, the small molecules of therapeutic agent may comprise a tyrosine kinase inhibitor.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™) sorafenib (Nexavar™), axitinib, or pazopanib.

The therapeutic agent may comprise a therapeutic agent suitable for treatment of dry AMD such as one or more of Sirolimus™ (rapamycin), Copaxone™ (glatiramer cetate), Othera™ Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; EYELEA (VEGF Trap) or complement inhibitor (POT-4).

The therapeutic agent may comprise a kinase inhibitor such as one or more of BIBW 2992 (small molecule targeting EGFR/Erb2), imatinib (small molecule), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2, VEGFR3, and/or FGFR1, small molecule commercially available from Esai, Co.). The therapeutic agent may comprises antibody drugs, e.g. bevacizumab, trastuzumab, cetuximab, and panitumumab.

Therapeutic agents may include various classes of drugs. Drugs include, for instance, steroids, non-steroidal anti-inflammatory drugs (NSAIDS), anti-cancer drugs, antibiotics, an anti-inflammatory (e.g., diclofenac), a pain reliever (e.g., bupivacaine), a calcium channel blocker (e.g., nifedipine), an antibiotic (e.g., ciprofloxacin), a cell cycle inhibitor (e.g., simvastatin), a protein (e.g., insulin). Therapeutic agents include classes of drugs including steroids, NSAIDS, antioxidants, antibiotics, pain relievers, inhibitors of vascular endothelial growth factor (VEGF), chemotherapeutics, anti-viral drugs, for instance. Examples of NSAIDS are ibuprofen, meclofenamate sodium, mefanamic acid, salsalate, sulindac, tolmetin sodium, ketoprofen, diflunisal, piroxicam, naproxen, etodolac, flurbiprofen, fenoprofen calcium, indomethacin, celoxib, ketorolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides of various molecular weights. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

The systems disclosed herein cab ne used to treat ocular diseases including but not limited to AMD, glaucoma, dry eye, allergic conjunctivitis and pain and inflammation following cataract surgery.

The therapeutic agents may be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (ciprofloxacin HCl opthalmic solution) may be used to treat infections caused by susceptible strains of microorganisms. NATACYN (natamycin opthalmic suspension) may be used for treatment of fungal blepharitis, conjunctivitis, and keratitis. NEVANAC (nepanfenac opthalmic suspension) may be used for treatment of pain and inflammation associated with cataract surgery. TRAVATAN (travoprost ophthalmic solution) may be used for reduction of elevated intraocular pressure-open-angle glaucoma or ocular hypertension. FML FORTE (fluorometholone ophthalmic suspension) may be used for treatment of corticosteroid-responsive inflammation of the palperbral and bulbar conjunctiva, cornea and anterior segment of the globe. LUMIGAN (bimatoprost ophthalmic solution) may be used for reduction of elevated intraocular pressure-open-angle glaucoma or ocular hypertension. PRED FORTE (brednisolone acetate) may be used for treatment of steroid-responsive inflammation of the palpebral and bulbar conjunctiva, cornea and anterior segment of the globe. PROPINE (dipivefrin hydrochloride) may be used for control of intraocular pressure in chronic open-angle glaucoma. RESTASIS (cyclosporine ophthalmic emulsion) may be used to increases tear production in patients, e.g., those with ocular inflammation associated with keratoconjunctivitis sicca. ALREX (loteprednol etabonate ophthalmic suspension) may be used for temporary relief of seasonal allergic conjunctivitis. LOTEMAX (loteprednol etabonate ophthalmic suspension) may be used for treatment of steroid-responsive inflammation of the palpebral and bulbar conjunctiva, cornea and anterior segment of the globe. MACUGEN (pegaptanib sodium injection) may be used for Treatment of neovascular (wet) age-related macular degeneration. OPTIVAR (azelastine hydrochloride) may be used for treatment of itching of the eye associated with allergic conjunctivitis. XALATAN (latanoprost ophthalmic solution) may be used to reduce elevated intraocular pressure in patients, e.g., with open-angle glaucoma or ocular hypertension. BETIMOL (timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of therapeutic agents for delivery include those that specifically bind a target peptide in vivo to prevent the interaction of the target peptide with its natural receptor or other ligands. AVASTIN, for instance, is an antibody that binds VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non-specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. VKC and AKC are chronic allergic diseases where cosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis. Permeation agents are agents and may also be included in a gel, hydrogel, organogel, xerogel, and biomaterials as described herein. These are agents that assist in permeation of a drug into an intended tissue. Permeation agents may be chosen as needed for the tissue, e.g., permeation agents for skin, permeation agents for an cardrum, permeation agents for an eye.

The agent may be treatment of a back of the eye disease, e.g., wherein the back of the eye disease is age-related macular degeneration (AMD) cystoid macular edema (CME), diabetic macular edema (DME), posterior uveitis, and diabetic retinopathy, or glaucoma.

The agents may be, e.g., an agent comprises anti-VEGF, blocks VEGFR1, blocks VEGFR2, blocks VEGFR3, anti-PDGF, anti-PDGF-R blocks PDGFRB, an anti-angiogenic agent, sunitinib, E7080, Takeda-6d, tivozanib, regorafenib, sorafenib, pazopanib, axitinib, nintedanib, cediranib, vatalanib, motesanib, macrolides, sirolimus, everolimus, tyrosine kinase inhibitors (TKIs), imatinibn gefinitib, toceranib, erlotinib, lapatinib, nilotinib, bosutinib neratinib, lapatinib, vatalanib, comprises low-soluble prostaglandin analogues for glaucoma, nepafenac, macrolides, rapamycin, sirolimus, tacrolimus, or serves to block mTOR receptors for AMD (also known as choroidal neovascularization (CNV). mTOR refers to mammalian target of rapamycin. Agents may be, e.g., moxifloxacin, dexamethasone, travoprost, steroids, fluoroquinolones, prostaglandin analogs, prostamides.

Ocular diseases include ocular pathologies, with hyphema, ocular hypertension, and glaucoma being conditions for treatment with an anterior chamber depot. Many agents are suitable for ocular delivery, e.g., NSAIDs, steroids, anti-glaucoma drugs, antivirals, antibiotics, mydriatics, and antifungals administered via intracameral injections.

Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other ocular conditions may be provided by delivery of agents from an implant.

The preceding description sets forth numerous specific details such as examples of specific systems, components, methods, and so forth in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular implementations may vary from these exemplary details and still be contemplated to be within the scope of the present disclosure.

Reference throughout this specification to "one embodiment," "an embodiment," or "some embodiments" means that a particular feature, structure, or characteristic described in connection with the embodiment is included in at least one embodiment. Thus, the appearances of the phrase "in one embodiment," "in an embodiment," or "in some embodiments" in various places throughout this specification are not necessarily all referring to the same embodiment. In addition, the term "or" is intended to mean an inclusive "or" rather than an exclusive "or." When the term "about" or "approximately" is used herein, this is intended to mean that the nominal value presented is precise within ±10%.

Although the operations of the methods herein are shown and described in a particular order, the order of operations of each method may be altered so that certain operations may be performed in an inverse order so that certain operations may be performed, at least in part, concurrently with other operations. In another embodiment, instructions or sub-operations of distinct operations may be in an intermittent and/or alternating manner.

It is understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A tip structure of an intracanalicular injectable applicator device, wherein the tip structure comprises:

a first distal end that attaches to a body of the intracanalicular injectable applicator device;

an inner surface forming a recess that receives a first cannula distal end of a cannula of the intracanalicular injectable applicator device, wherein a second cannula distal end of the cannula is coupled to the body; and a second distal end comprising a beveled tip configured to be inserted in a lacrimal punctum to dilate the lacrimal punctum and to inject an intracanalicular injectable from the cannula into a canaliculus via the lacrimal punctum.

2. The tip structure of claim 1, wherein the tip structure has a Shore A durometer of about 50 to about 120, and wherein an opening of the second distal end of the tip structure has a diameter that is smaller than an outer diameter of the intracanalicular injectable.

3. The tip structure of claim 1, wherein the second distal end of the tip structure has a length of about 1 to 5 mm, and a diameter of the second distal end is about 0.1 to 0.4 mm.

4. The tip structure of claim 1, wherein the intracanalicular injectable comprises travoprost, cyclosporine or dexamethasone.

5. A system comprising:

an intracanalicular injectable applicator device comprising:

a body forming a cavity;

a cannula coupled to a first distal end of the body, wherein the cannula forms a channel that is aligned with the cavity of the body;

a tip structure coupled to the body, wherein the tip structure is disposed around at least a portion of the cannula, wherein a distal end of the tip structure is configured to dilate a lacrimal punctum by inserting the distal end of the tip structure into a canaliculus via the lacrimal punctum; and an actuating structure; and an intracanalicular injectable loaded in the channel of the cannula of the intracanalicular injectable applicator device, wherein the actuating structure is configured to push the intracanalicular injectable through the channel and the distal end of the tip structure into the canaliculus via the lacrimal punctum while the distal end of the tip structure is inserted into the canaliculus via the lacrimal punctum.

6. A kit comprising:

an enclosure to house a plurality of components, the plurality of components comprising:

an intracanalicular injectable applicator device comprising:

a body forming a cavity;

a cannula coupled to a first distal end of the body, wherein the cannula forms a channel that is aligned with the cavity of the body, and wherein the cannula is configured to store an intracanalicular injectable in the channel;

a tip structure coupled to the body, wherein the tip structure is disposed around at least a portion of the cannula, wherein a distal end of the tip structure is configured to dilate a lacrimal punctum by inserting the distal end of the tip structure into a canaliculus via the lacrimal punctum; and an actuating structure configured to push the intracanalicular injectable through the channel and the distal end of the tip structure into the canaliculus via the lacrimal punctum while the distal end of the tip structure is inserted into the canaliculus via the lacrimal punctum; and the intracanalicular injectable.

7. The kit of claim 6, wherein the enclosure is a foil pouch, and wherein the plurality of components further comprises a desiccant.

8. The kit of claim 6, wherein the intracanalicular injectable is loaded into the intracanalicular injectable applicator device in the kit.

9. The kit of claim 6, wherein the intracanalicular injectable comprises travoprost, cyclosporine or dexamethasone.

10. The kit of claim 6, wherein the distal end of the tip structure has a Shore A durometer of about 50 to about 120, and wherein an opening of the distal end of the tip structure has a diameter that is smaller than an outer diameter of the intracanalicular injectable.

11. The kit of claim 6, wherein the actuating structure comprises:

a plunger structure configured to be disposed at least partially in the cavity of the body, wherein a first distal end of the plunger structure is configured to receive a force to cause actuation of the actuating structure; and a push-wire, wherein a first distal end of the push-wire is attached to a second distal end of the plunger structure, wherein a second distal end of the push-wire is disposed in the channel of the cannula prior to the actuation of the actuating structure, wherein the push-wire is configured to push the intracanalicular injectable through the channel responsive to the actuation of the actuating structure.

12. The kit of claim 11, wherein the plunger structure comprises hooked clips configured to insert into corresponding recesses formed by an outer surface of the body to prevent the plunger structure and the body from separating and to constrain movement of the intracanalicular injectable in the cannula.

13. The kit of claim 11, wherein:

a portion of the plunger structure disposed in the cavity of the body has a non-circular perimeter;

a portion of the cavity of the body has a non-circular profile that corresponds to the non-circular perimeter; and the actuating structure is to be rotated to align the non-circular perimeter of the portion of the plunger structure with the non-circular profile of the portion of the cavity of the body to actuate the actuating structure.

14. The kit of claim 11, wherein at least one of:

the cannula is affixed to the body via adhesion or insert molding, wherein the second distal end of the plunger structure forms a slot, wherein the push-wire is adhered or insert molded into the slot; or the cavity of the body and an outer profile of the plunger structure are tapered to direct the push-wire into the cannula.

15. The system of claim 5, wherein the intracanalicular injectable comprises travoprost, cyclosporine or dexamethasone.

16. The system of claim 5, wherein the distal end of the tip structure has a Shore A durometer of about 50 to about 120, and wherein an opening of the distal end of the tip structure has a diameter that is smaller than an outer diameter of the intracanalicular injectable.

17. The system of claim 5, wherein the actuating structure comprises:

a plunger structure configured to be disposed at least partially in the cavity of the body, wherein a first distal end of the plunger structure is configured to receive a force to cause actuation of the actuating structure; and a push-wire, wherein a first distal end of the push-wire is attached to a second distal end of the plunger structure, wherein a second distal end of the push-wire is disposed in the channel of the cannula prior to the actuation of the actuating structure, wherein the push-wire is configured to push the intracanalicular injectable through the channel responsive to the actuation of the actuating structure.

18. The system of claim 17, wherein the plunger structure comprises hooked clips configured to insert into corresponding recesses formed by an outer surface of the body to prevent the plunger structure and the body from separating and to constrain movement of the intracanalicular injectable in the cannula.

19. The system of claim 17, wherein:

a portion of the plunger structure disposed in the cavity of the body has a non-circular perimeter;

a portion of the cavity of the body has a non-circular profile that corresponds to the non-circular perimeter; and the actuating structure is to be rotated to align the non-circular perimeter of the portion of the plunger structure with the non-circular profile of the portion of the cavity of the body to actuate the actuating structure.

20. The system of claim 17, wherein at least one of:

the cannula is affixed to the body via adhesion or insert molding, wherein the second distal end of the plunger structure forms a slot, wherein the push-wire is adhered or insert molded into the slot; or the cavity of the body and an outer profile of the plunger structure are tapered to direct the push-wire into the cannula.

* * * * *